US012329756B2

(12) United States Patent
Dussor et al.

(10) Patent No.: US 12,329,756 B2
(45) Date of Patent: *Jun. 17, 2025

(54) REGULATION OF EIF4E ACTIVITY FOR MIGRAINE THERAPY

(71) Applicant: Board of Regents, The University of Texas System, Austin, TX (US)

(72) Inventors: Greg Dussor, Dallas, TX (US); Jacob E. Lackovic, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/428,087

(22) Filed: Jan. 31, 2024

(65) Prior Publication Data

US 2025/0017926 A1    Jan. 16, 2025

Related U.S. Application Data

(63) Continuation of application No. 17/495,902, filed on Oct. 7, 2021, now Pat. No. 11,925,642.

(60) Provisional application No. 63/089,326, filed on Oct. 8, 2020.

(51) Int. Cl.
| | |
|---|---|
| *A61K 31/506* | (2006.01) |
| *A61K 31/05* | (2006.01) |
| *A61K 31/167* | (2006.01) |
| *A61K 31/19* | (2006.01) |
| *A61K 31/343* | (2006.01) |
| *A61K 31/426* | (2006.01) |

(52) U.S. Cl.
CPC .......... *A61K 31/506* (2013.01); *A61K 31/05* (2013.01); *A61K 31/167* (2013.01); *A61K 31/19* (2013.01); *A61K 31/343* (2013.01); *A61K 31/426* (2013.01)

(58) Field of Classification Search
CPC ... A61K 31/343; A61K 31/426; A61K 31/506
See application file for complete search history.

(56) References Cited

U.S. PATENT DOCUMENTS

| | | | | |
|---|---|---|---|---|
| 11,925,642 | B2 * | 3/2024 | Dussor | A61K 31/05 |
| 2015/0376181 | A1 | 12/2015 | Reich et al. | |
| 2020/0131179 | A1 | 4/2020 | Reich et al. | |

FOREIGN PATENT DOCUMENTS

| | | |
|---|---|---|
| WO | WO 2017/117052 | 6/2017 |
| WO | WO 2018/218038 | 11/2018 |
| WO | WO2020/155842 | 8/2020 |

OTHER PUBLICATIONS

Burgos-Vega, C. C. et al., "Non-invasive dural stimulation in mice: A novel preclinical model of migraine," Cephalalgia, 39.1 (2019): 123-134.
Furukawa et al., "(−)-Cercosporamide derivatives as novel antihyperglycemic agents", Bioorganic & Medicinal Chemistry Letters, 19(3): 724-726, 2009.
Gkogkas et al (2013) Autism-related deficits via dysregulated eIF4E-dependent translational control. Nature 493 371 PMID: 23172145.
Harriott et al., "Animal models of migraine and experimental techniques used to examine trigeminal sensor processing", The Journal of Headache and Pain, 20:91, 2019.
Hou., et al. "Targeting Mnks for cancer therapy", Oncotarget, 3(2), 118-131 (2012).
International Preliminary Report on Patentability for PCT/US2021/039982 dated Dec. 13, 2022, 8 pages.
International Search Report and Written Opinion for PCT/US21/39982 dated Dec. 23, 2021, 11 pages.
International Search Report and Written Opinion for PCT/US22/35703 dated Nov. 16, 2022, 14 pages.
Jeevakumar et al., "IL-6 induced upregulation of T-type $Ca^{2+}$ currents and sensitization of DRG nociceptors is attenuated by MNK inhibition", J Neurophysiol, 124(1):274-283, 2020.
Khoutorsky et al., "Translational control of nociception via 4E-binding protein 1", Elife, 2015; 4: e12002.
Khoutorsky et al., "Translational control mechanisms in persistent pain", Trends Neurosci, 41: 100-114, 2018.
Konicek et al., "Therapeutic inhibition of MAP kinase interacting kinase blocks eukaryotic initiation factor 4E phosphorylation and suppresses outgrowth of experimental lung metastases", Cancer Research, 71(5): 1849-1857 (2011).
Lackovic et al "IHC 2019 Abstracts" received from https://journals.sagepub.com/doi/10.1177/0333102419859835, 2019.
Lackovic et al. "De novo protein synthesis is necessary for priming in preclinical models of migraine." Poster—Society for Neuroscience, 2019.
Lackovic et al., "De novo protein synthesis is necessary for priming in preclinical models of migraine", Cephalalgia, 41(2):237-246, 2021.
Melemedjian et al., "IL-6- and NGF-induced rapid control of protein synthesis and nociceptive plasticity via convergent signaling to the eIF4F complex", J Neurosci., 30: 15113-15123, 2010.

(Continued)

Primary Examiner — James D. Anderson
(74) Attorney, Agent, or Firm — Parker Highlander PLLC

(57) ABSTRACT

The present disclosure provides a method of preventing, treating, or inhibiting migraine in a subject, by administering to the subject an amount of first therapeutic selected from cercosporamide, eFT508, or 4EGI-1 sufficient to prevent, treat, or inhibit said migraine. The present disclosure further provides a composition including at least two of cercosporamide, eFT508, or 4EGI-1, both in an amount sufficient to prevent, treat, or inhibit migraine in a subject and a pharmaceutically acceptable carrier. The present disclosure further provides a composition including at least one of cercosporamide, eFT508, or 4EGI-1 and at least one additional migraine therapeutic, both in an amount sufficient to prevent, treat, or inhibit migraine in a subject, and a pharmaceutically acceptable carrier.

18 Claims, 10 Drawing Sheets

(56) References Cited

OTHER PUBLICATIONS

Mitsikostas et al., "The 5-HT1F receptor as the target of ditans in migraine—from bench to bedside", *Nature Reviews Neurology*, 19(8):498-505, 2023.

Mody et al., "eIF4E phosphorylation modulates pain and neuroinflammation in the aged", *Geroscience*, 42(6):1663-1674, 2020.

Moerke et al., "Small-molecule inhibition of the interaction between the translation initiation factors eIF4E and eIF4G", *Cell*, 128:257-267, 2007.

Moy et al., "eIF4E phosphorylation influences Bdnf mRNA translation in mouse dorsal root ganglion neurons", *Front Cell Neurosci*, 12:29, 2018.

Moy et al., "The MNKeIF4E signaling axis contributes to injury-induced nociceptive plasticity and the Development of chronic pain", *J Neurosci.*, 37: 7481-7499, 2017.

Plessas et al., "Migraine-like Episodic Pain Behavior in a Dog: Can Dogs Suffer from Migraines?", *J. Vet Intern Med.*, 27:1034-1040, 2013.

Price et al., "Translation regulation and pain special issue editorial for neurobiology of pain", *Neurobiol Pain*, 4: 1, 2018.

Price et al., "Reversal of peripheral nerve injury-induced neuropathic pain and cognitive dysfunction via genetic and tomivosertib targeting of MNK", *Neuropsychopharmacology*, 45(3) 524-533, 2020.

Price et al., Pharmacological manipulation of translation as a therapeutic target for chronic pain. *Pharmacological Reviews*. 73(1) 59-88, 2021.

Pubchem CID 139317491, create date Nov. 2, 2019, date accessed Jul. 7, 2023, 10 pages.

Pubmed Compound Record for CID 118598717, '6-[(6-Aminopyrimidin-4-yl)amino]-3-(3-fluorophenyl)-3,8-dimethyl-2H-imidazo[1,5-a]pyridine-1,5-dione', U.S. National Library of Medicine, Feb. 23, 2016, pp. 1-8.

Pubmed Compound Record for CID 144985837, 'Tert-butyl N-[6-[(8-methyl-1, 5-dioxo-3,3-dipropyl-2H-imidazo(1,5-a]pyridine-6-yl)amino]pyrimidine-4-yl]carbamate', U.S. National Library of Medicine, Dec. 7, 2019, pp. 1-6.

Rissardo et al., "Gepants for Acute and Preventive Migraine Treatment: A Narrative Review", *Brain Sciences*, 12, 1612, 2022.

Shukla et al., "A Highly Selective MNK Inhibitor Rescues Deficits Associated with Fragile X Syndrome in Mice", *Neurotherapeutics*, 18(1):624-639, 2021.

Shiers et al., "Reversal of peripheral nerve injury-induced neuropathic pain and cognitive dysfunction via genetic and tomivosertib targeting of MNK", *Neuropsychopharmacology*, 45(3) 524-533, 2020.

Sussman et al., "Discovery of cercosporamide, a known antifungal natural product, as a selective Pkc1 kinase inhibitor through high-throughput screening", *Eukaryot.Cell*, 3(4):932-943, (2004).

Yousuf et al., "Pharmacological manipulation of translation as a therapeutic target for chronic pain", *Pharmacological Reviews*, 73(1) 59-88, 2021.

\* cited by examiner

REGULATION OF EIF4E ACTIVITY FOR MIGRAINE THERAPY

PRIORITY CLAIM

This application is a continuation of U.S. Non-Provisional patent application Ser. No. 17/495,902, filed Oct. 7, 2021, entitled "REGULATION OF eIF4E ACTIVITY FOR MIGRAINE THERAPY," which claims benefit of priority to U.S. Provisional Application Ser. No. 63/089,326, filed Oct. 8, 2020, the entire contents of which are hereby incorporated by reference.

FEDERAL FUNDING STATEMENT

This invention was made with government support under grant no. R01 NS072204 awarded by the National Institutes of Health. The government has certain rights in the invention.

BACKGROUND

1. Field

This disclosure relates to the fields of medicine and cell biology. More specifically, it relates to the use of the MNK inhibitor eFT508 to treat pain, either as a stand-alone therapeutic option, or in combination with other pain therapies.

2. Related Art

Migraine attacks are often triggered by normally innocuous stimuli, suggesting that sensitization within the nervous system is present. One mechanism that may contribute to neuronal sensitization in this context is translation regulation of new protein synthesis. The goal of this study was to determine whether protein synthesis contributes to behavioral responses and priming in preclinical models of migraine.

SUMMARY

The present disclosure provides a method of preventing, treating, or inhibiting migraine in a subject, by administering to the subject an amount of first therapeutic selected from cercosporamide, eFT508, or 4EGI-1 sufficient to prevent, treat, or inhibit said migraine. The first therapeutic may be delivered to the subject daily, or upon onset of at least one migraine symptom in the subject.

The method may further include additionally administering to the subject a second therapeutic selected from cercosporamide, eFT508, 4EGI-1, a CGRP inhibitor, a gepant, a ditan, a triptan, an ergotamine, an antiemetic, a NSAID or a non-narcotic analgesic, an opiate analgesic, a nonopoate analgesic, a steroid, lidocaine; valproic acid; or propofol.

The first therapeutic and second therapeutic may be co-formulated and may be delivered to the subject daily or upon onset of at least one migraine symptom in the subject.

The first therapeutic and second therapeutic may not be co-formulated and may be delivered to the subject at the same time or at distinct times. One of the first therapeutic or second therapeutic may be delivered to the subject daily, while the other of the first therapeutic or second therapeutic may be delivered to the subject upon onset of at least one migraine symptom in the subject. The first and second therapeutics may both be delivered to the subject daily. The first and second therapeutics may both be delivered to the subject upon onset of at least one migraine symptom in the subject.

The subject may be a human. The subject may have previously experienced migraine.

The first therapeutic may suppress or inhibit translation of at least one eIF4E-dependent mRNA in the subject, suppress or inhibit eIF4E activity in the subject, suppress or inhibit phosphorylation of 4E-BP or Ser209 of eIF4E in the subject, and/or suppress or inhibit MNK activity in the subject.

The disclosure further provides a composition including at least two of cercosporamide, eFT508, or 4EGI-1, both in an amount sufficient to prevent, treat, or inhibit migraine in a subject, and a pharmaceutically acceptable carrier.

The disclosure further provides a composition including at least one of cercosporamide, eFT508, or 4EGI-1 and at least one additional migraine therapeutic, both in an amount sufficient to prevent, treat, or inhibit migraine in a subject, and a pharmaceutically acceptable carrier.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

and male (FIG. 4B) eIF4E$^{S209A}$ mice after injection of dural IL-6 and dural pH 7.0. For FIG. 4A n=8 for WT groups; n=7 for 4EKI/SIF and n=8 for 4EKI/IL-6. For FIG. 4B n=8 for WT/SIF and 4EKI/IL-6; n=7 for WT/IL-6 and 4EKI/SIF. Analysis of groups was performed using two-way ANOVA followed by Bonferroni post-hoc test (see Table 1 for F-values). *p<0.05, p<0.01, *p<0.001, ****p<0.0001.

Figure 5A:
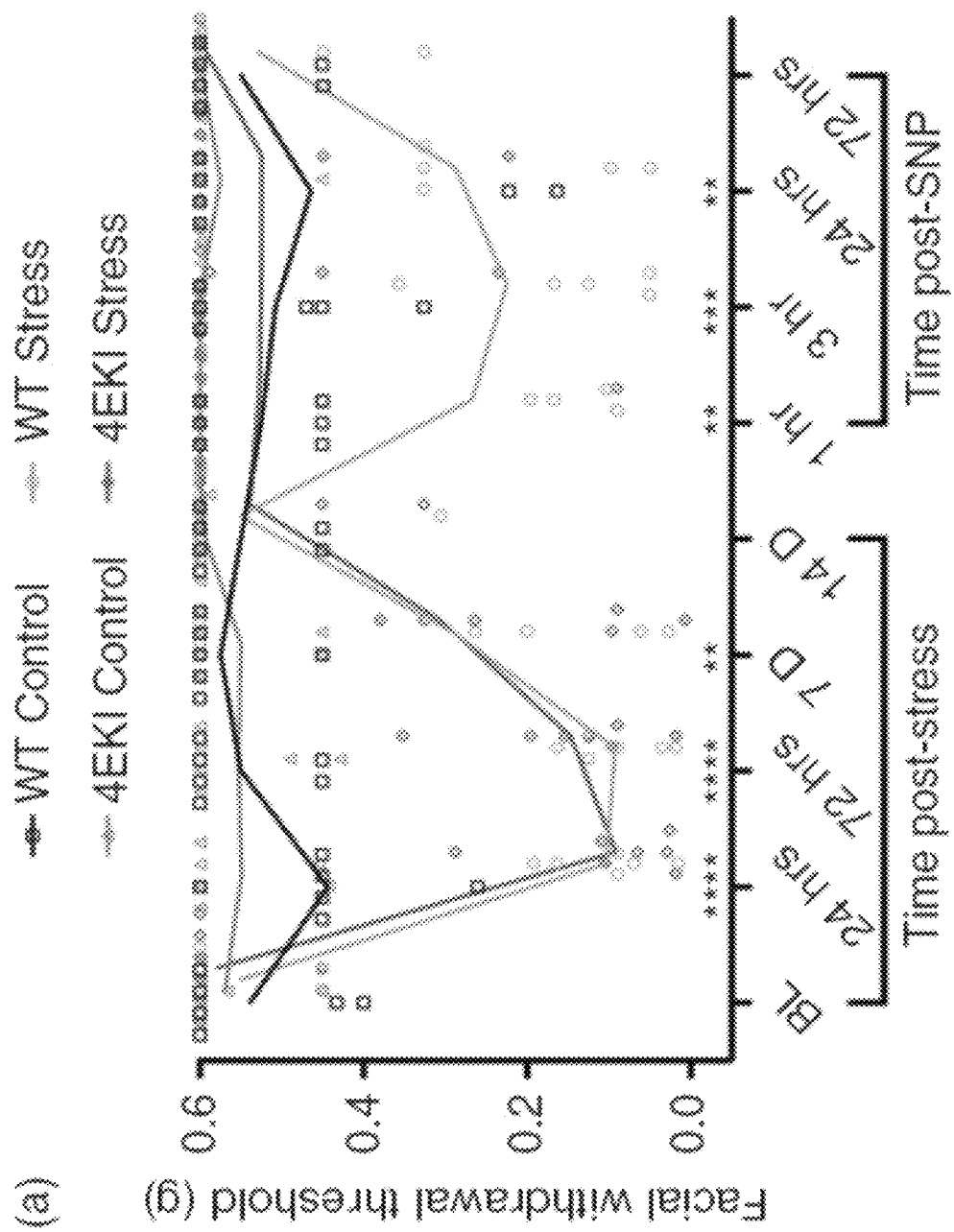
Figure 5B:
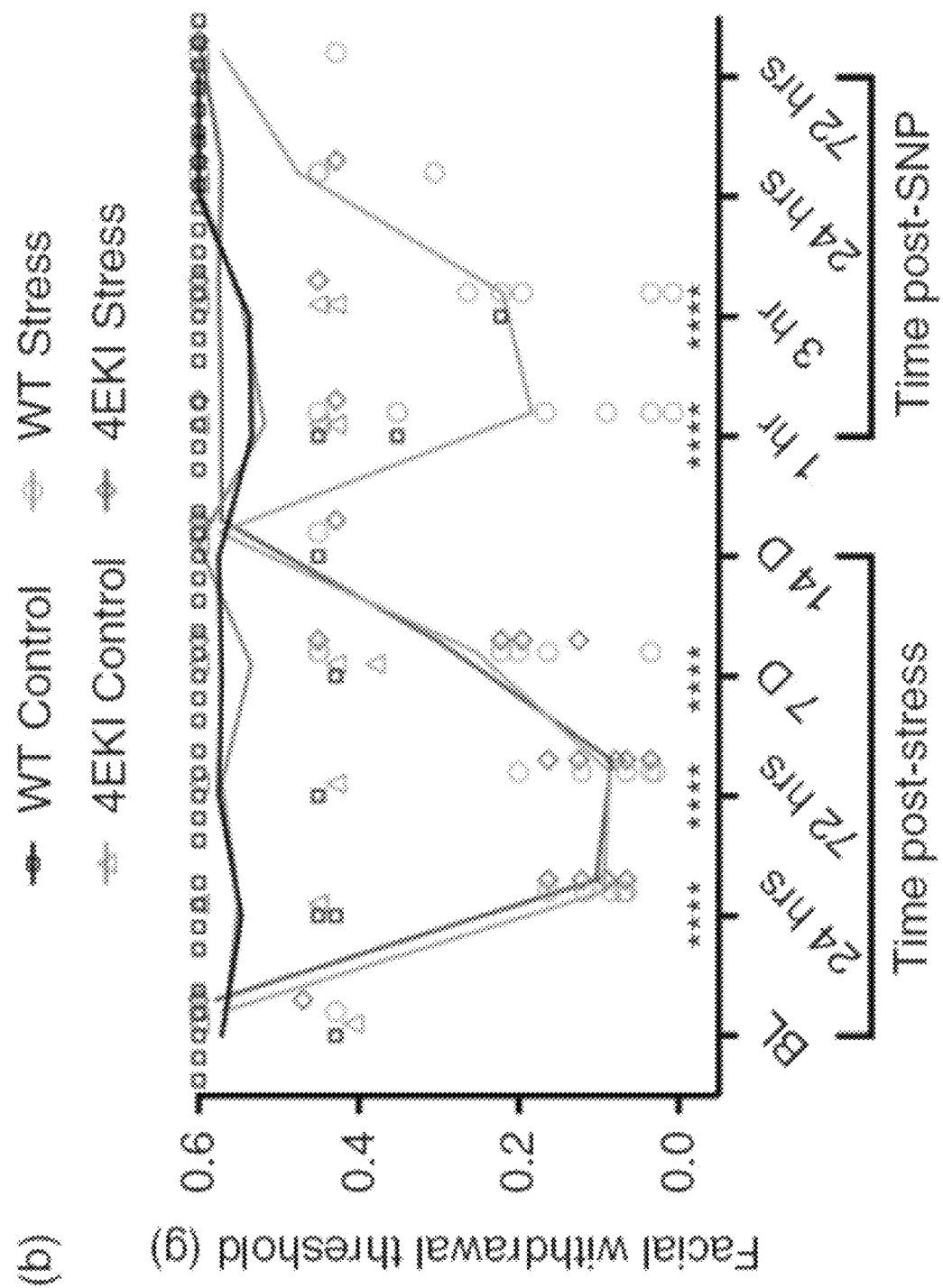

FIGS. 5A-5B show results related to regulation of phosphorylation of eIF4E after repeated restraint stress. The graphs show facial withdrawal threshold effects in female (FIG. 5A) and male (FIG. 5B) eIF4E$^{S209A}$ mice and WT mice following repeated restraint stress or a sub-threshold dose of the nitric oxide donor SNP (n≥6). For FIG. 5A, n=6 for all groups except 4EKI/Stress, for which n=7. For FIG. 5B, n=6 for all groups. Analysis of groups was performed using two-way ANOVA followed by Bonferroni post-hoc test (see Table 1 for F-values). *p<0.05, p<0.01, *p<0.001, ****p<0.0001.

Figures 6A, 6B:
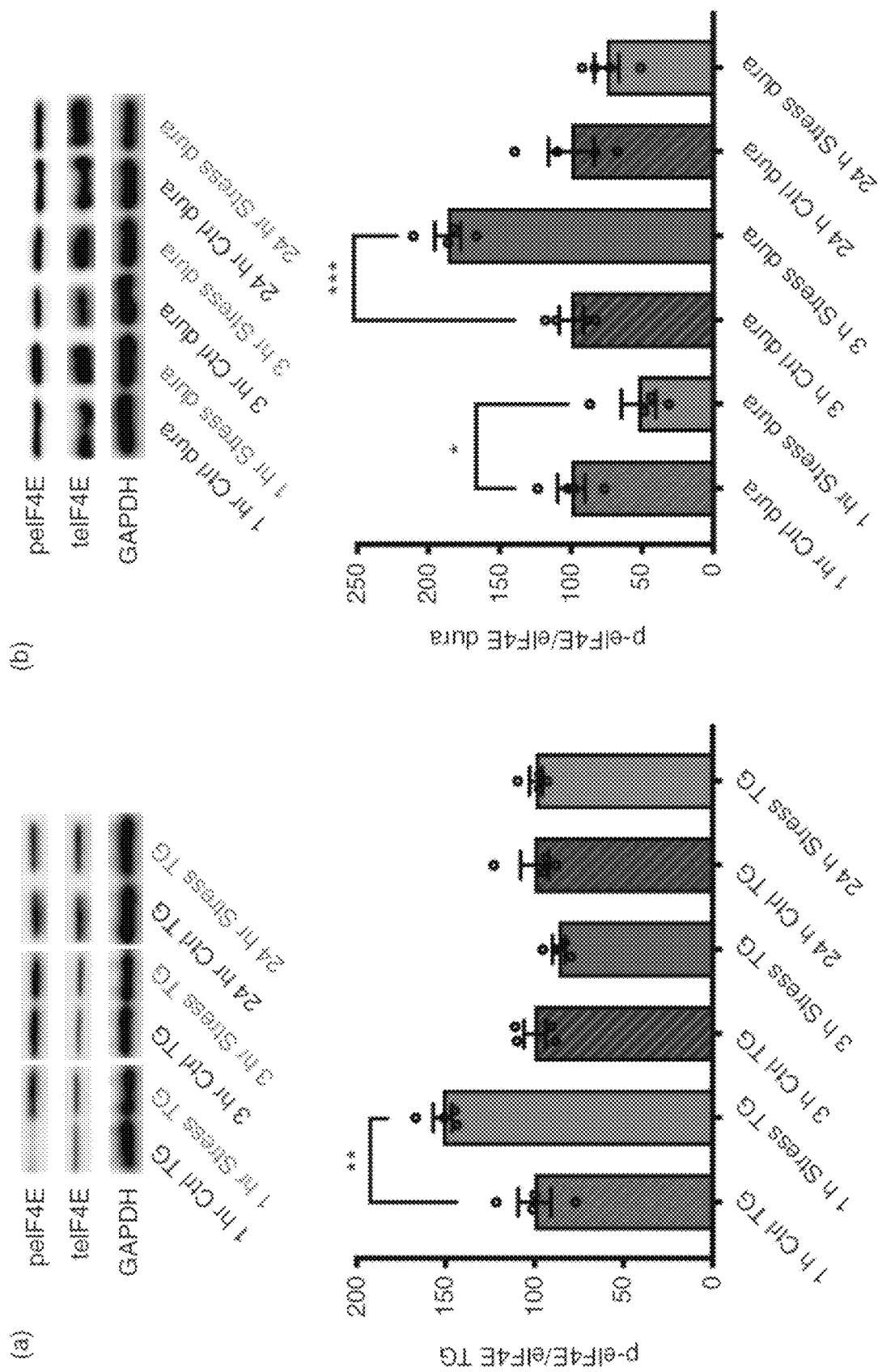

FIGS. 6A-6B show results related to the time points at which eIF4E phosphorylation is altered in response to stress. FIG. 6A is a Western blot of phosphorylated or unphosphorylated eIF4E in the trigeminal ganglia (TG) at various timepoints after stress and a graph of phosphorylated eIF4E to total eIF4E in the TG at various timepoints after stress. FIG. 6B is a Western blot of phosphorylated or unphosphorylated eIF4E in the dura at various timepoints after stress and a graph of phosphorylated eIF4E to total eIF4E in the TG at various timepoints after stress. N=4 mice pooled for each time point. GAPDH was used as a loading control. Significance between treatments was determined via Student's unpaired two-tailed t-test. Data are represented as means±SEM. *p<0.05, **p<0.01. *p<0.001.

Figure 7A:
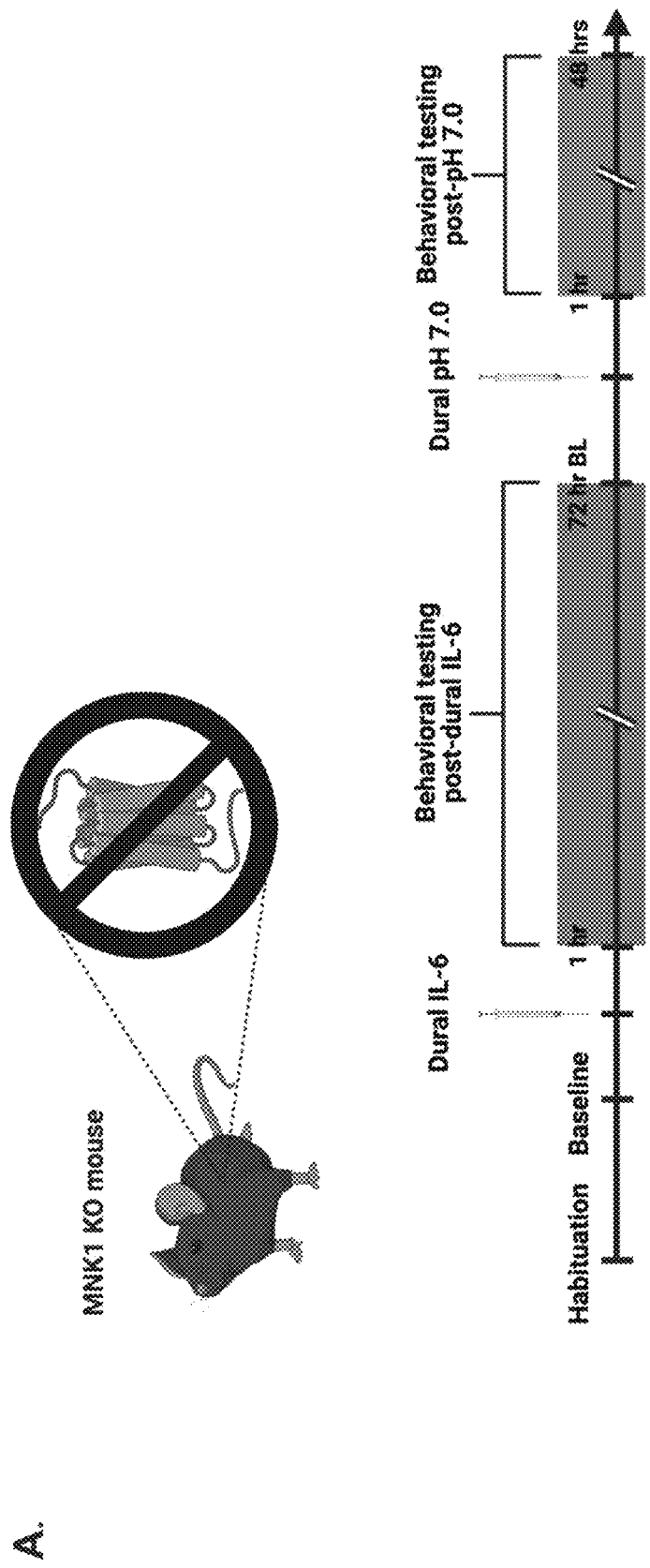
Figure 7B:
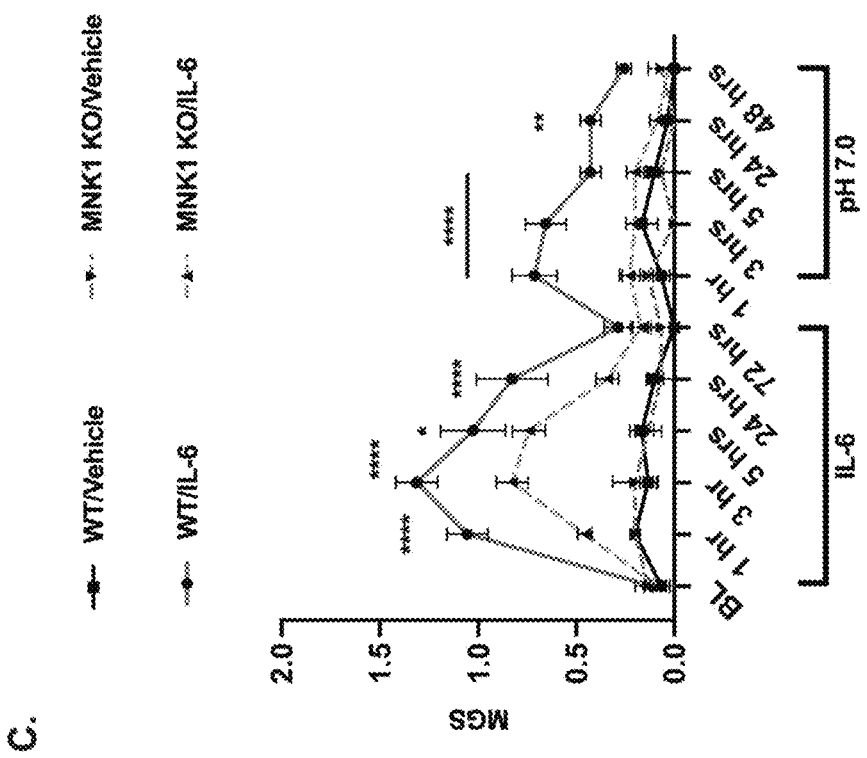
Figure 7C:
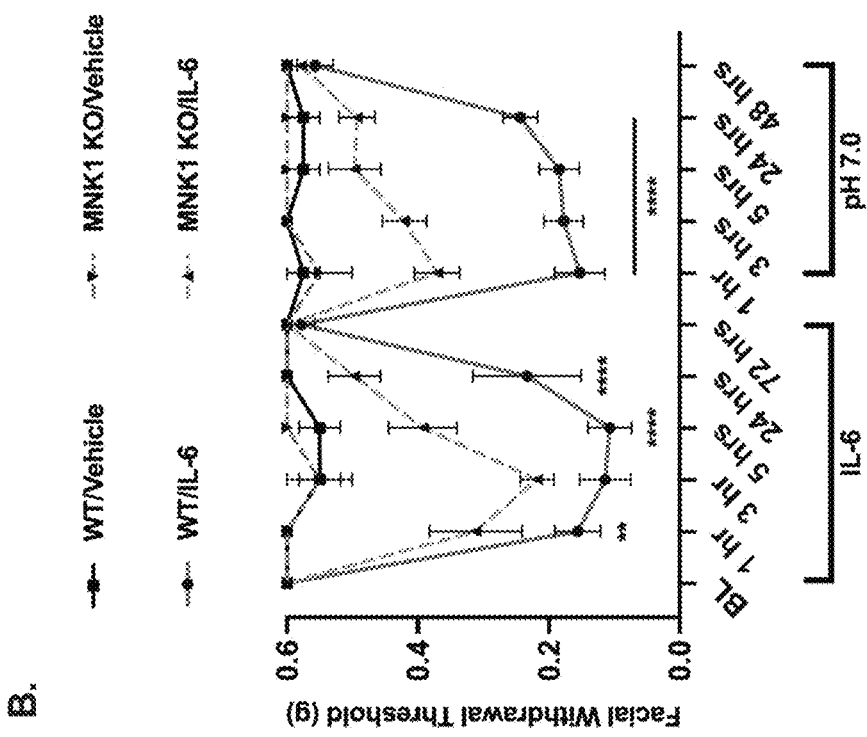

FIGS. 7A-7C shows results related to the role of genetic inhibition of MNK in facial hypersensitivity and hyperalgesic priming caused by dural IL-6. FIG. 7A is a schematic diagram of the testing protocol using male and female wild-type (WT) C57/BL6 and MNK1 KO mice. FIG. 7B is a graph showing the facial withdrawal thresholds (von Frey thresholds) in wild type and MNK1 KO mice following dural IL-6 injection or and in those that were not primed (vehicle). FIG. 7C is a graph showing the mean grimace scores (MGS) in wild type and MNK1 KO mice following dural IL-6 injection, synthetic interstitial fluid pH 7.0, or no treatment (vehicle). A similar effect was observed in grimace measurements, in which MNK1 KO mice had significantly lower mean grimace scores (MGS) compared to WT mice following dural IL-6 injection, synthetic interstitial fluid pH 7.0, or no treatment (vehicle). * denotes significance between MNK1 KO/IL-6 and WT/IL-6 groups. For all groups, n=3-7. Data are represented as mean±SEM. *p<0.05, p<0.01, **p<0.0001.

DESCRIPTION OF ILLUSTRATIVE EMBODIMENTS

The present disclosure provides methods of treating, preventing, or inhibiting migraine in a subject, particularly a human.

1. Migraine

A distinct characteristic of migraine patients is their enhanced sensitivity to innocuous stimuli, which can trigger and exacerbate a migraine headache (1, 2). In preclinical models of migraine, repetitive stimulation of dural afferents not only contributes to peripheral plasticity, but also to central plasticity at synapses in the trigeminal nucleus caudalis (TNC), which is thought to account for the cutaneous facial allodynia present in humans during attacks (3,4). Activation of meningeal afferents results in the release of numerous pro-inflammatory cytokines, growth factors, excitatory neurotransmitters, and neuropeptides from primary sensory neurons, degranulated mast cells, and dural fibroblasts (5-8). Many of these endogenous factors, including IL-6 and calcitonin gene-related peptide (CGRP), directly contribute to the sensitization of primary sensory neurons as well as their downstream targets in the TNC (6, 8-13). Based on this, mechanisms underlying peripheral and central sensitization have been proposed to contribute to these symptoms.

Repeated or intense noxious stimulation can cause maladaptive changes in synaptic plasticity within nociceptive circuits, leading to peripheral and central sensitization (14). Nascent protein synthesis in response to noxious stimuli can induce long-term changes in nociceptor activity and gene expression that can lead to the development of chronic pain (15-19). Additionally, regulation of nascent protein synthesis via activity-dependent translation has been shown to be a highly critical molecular event for neuroplasticity and plays a key role in changing nociceptor functionality (17, 20-23). Activity-dependent translation can be induced by various endogenous compounds and membrane receptors and is regulated via the mammalian/mechanistic target of rapamycin complex 1 (mTORC1) and the extracellular-signal-regulated kinase (ERK) pathways, which converge on eukaryotic initiation factor 4E (eIF4E) of the eIF4E translation preinitiation complex. Interestingly, in the dorsal root ganglion and dorsal horn of the spinal cord, these pathways are robustly activated following peripheral nerve inflammation and nerve injury and have been demonstrated as being essential for the persistence of chronic pain. For example, inhibition of mTORC1, activity-dependent translation, or general translation by local administration of rapamycin, 4EGI-1, or anisomycin, respectively, reduces mechanical hypersensitivity and injury-induced changes in nociceptor excitability, further implicating mechanisms of translation in the maintenance of pain (22, 24).

2. MNKs

Mitogen-activated protein (MAP) kinases interacting kinases (MNKs) phosphorylate the eukaryotic translation initiation factor 4E (eIF4E) and factors that bind to AU-rich elements in the 3'-untranslated region of certain mRNAs. MNKs apparently regulate the expression of a specific set of proteins rather than global protein synthesis, and are involved in growth control, inflammation and viral translation. Therefore, they represent interesting targets for pharmaceutical intervention.

MNKs comprise a subfamily of Ser/Thr kinases, phylogenetically considered Ca2+/calmodulin-dependent kinases (CaMK). MNKs are activated through phosphorylation by the growth factor-stimulated Ras/extracellular signal-regulated kinase pathway and the stress-induced p38 pathway. There are two human MNK genes, mnk1 and mnk2, each of is alternatively spliced in to different isoforms (Mnk1a, Mnk1b, Mnk2a and Mnk2b) of 347-465 residues. All four proteins contain a stretch of basic residues at their N-termini that functions as a nuclear localization signal and as a binding region for the eukaryotic initiation factor 4G. Mnk1a and Mnk2a contain putative nuclear export motifs and MAP kinase-binding sites C-terminal of the central kinase domains, both of which are removed by alternative splicing in Mnk1b and Mnk2b.

3. eIF4F Involvement With MNK Signaling

Eukaryotic initiation factor 4F (eIF4F) is a heterotrimeric protein complex that binds the 5' cap of messenger RNAs (mRNAs) to promote eukaryotic translation initiation. The eIF4F complex is composed of three non-identical subunits: the DEAD-box RNA helicase eIF4A, the cap-binding protein eIF4E, and the large "scaffold" protein eIF4G. The mammalian eIF4E complex was first described in 1983 and has been a major area of study into the molecular mechanisms of cap-dependent translation initiation ever since. eIF4E is important for recruiting the small ribosomal subunit (40S) to the 5' cap of mRNAs during cap-dependent translation initiation. Components of the complex are also involved in cap-independent translation initiation; for instance, certain viral proteases cleave eIF4G to remove the eIF4E-binding region, thus inhibiting cap-dependent translation.

Structures of eIF4F components have been solved individually and as partial complexes by a variety of methods, but no complete structure of eIF4F is currently available. In mammals, the eIF4E•G•A trimeric complex can be directly purified from cells, while only the two subunit eIF4E•G can be purified from yeast cells. eIF4E binds the m7G 5' cap and the eIF4G scaffold, connecting the mRNA 5' terminus to a hub of other initiation factors and mRNA. The interaction of eIF4G•A is thought to guide the formation of a single-stranded RNA landing pad for the 43S preinitiation complex (43S PIC) via eIF4A's RNA helicase activity.

The eIF4E proteins interact with a number of different binding partners, and there are multiple genetic isoforms of eIF4A, eIF4E, and eIF4G in the human genome. In mammals, eIF4F is bridged to the 40S ribosomal subunit by eIF3 via eIF4G, while budding yeast lacks this connection. Interactions between eIF4G and PABP are thought to mediate the circularization of mRNA particles. The eIF4E subunit of eIF4E is an important target of mTOR signaling through the eIF4E binding protein (4E-BP). Phosphorylation of 4E-BPs by mTOR prevents their binding to eIF4E, freeing eIF4E to bind eIF4G and participate in translation initiation.

Hyperphosphorylation of the 4E-BPs by the mTOR kinase in response to a variety of environmental cues results in the release of eIF4E, allowing the cap-binding protein to associate with eIF4G and assemble an active eIF4F complex. In addition, the cap-binding protein eIF4E is phosphorylated by the eIF4G-associated kinase MNK-1.

It is known that inhibiting activity-dependent mRNA translation through mechanistic target of rapamycin and mitogen-activated protein kinase (MAPK) pathways blocks the development of nociceptor sensitization. These pathways convergently signal to the eukaryotic translation initiation factor (eIF) 4F complex to regulate the sensitization of nociceptors, but the details of this process are ill defined. Moy et al. (2017) (24) investigated whether the phosphorylation of eIF4E by its specific kinase MAPK interacting kinases (MNKs) ½ was involved in nociceptor sensitization and chronic pain. Phosphorylation of ser209 on eIF4E regulates the translation of a subset of mRNAs, and the authors showed that pronociceptive and inflammatory factors, such as nerve growth factor (NGF), interleukin-6 (IL-6), and carrageenan, produced decreased mechanical and thermal hypersensitivity, decreased affective pain behaviors, and strongly reduced hyperalgesic priming in mice lacking eIF4E phosphorylation (eIF4E$^{S209A}$). Moreover, in patch-clamp electrophysiology and $Ca^{2+}$-imaging experiments on dorsal root ganglion neurons, NGF- and IL-6-induced increases in excitability were attenuated in neurons from eIF4ES209A mice. These effects were recapitulated in Mnk1/2-/- mice and with the MNK1/2 inhibitor cercosporamide. The authors also found that cold hypersensitivity induced by peripheral nerve injury is reduced in eIF4ES209A and Mnk 1/2-/- mice and following cercosporamide treatment. They concluded that the MNK1/2-eIF4E signaling axis is an important contributing factor to mechanisms of nociceptor plasticity and the development of neuropathic pain.

4. Potential Mechanism of Action of eIF4E in Migraine

The present disclosure is based on novel evidence relating to translational regulation in the development and persistence of migraine headache obtained using a dural stimulation model and a repeated stress-induced hypersensitivity model in mice as presented in the Examples. This evidence establishes a role for de novo protein synthesis in the behavioral responses and priming in these mouse models of migraine.

Figure 1:
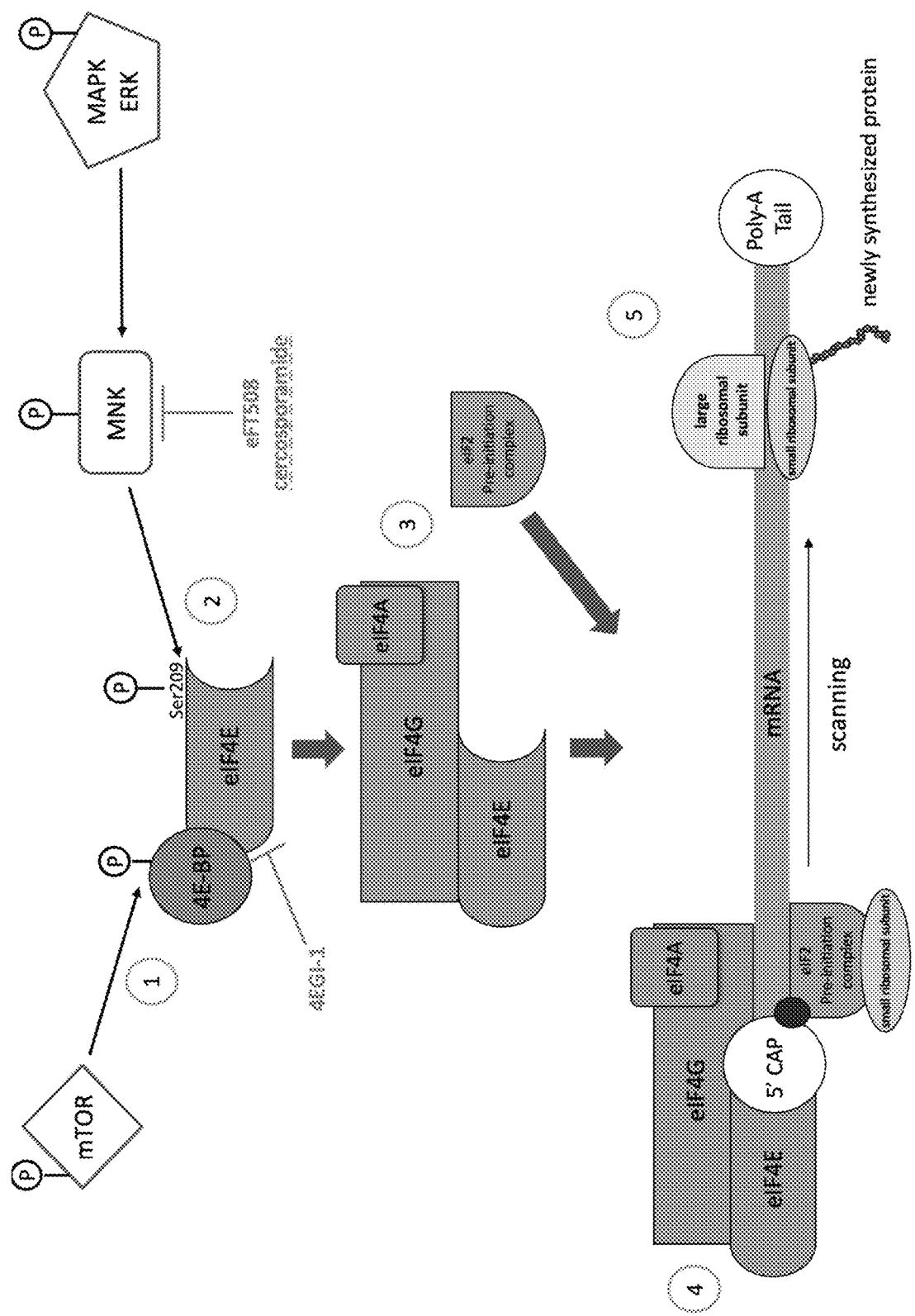
FIG. 1 shows a potential pathway for the role of eIF4E in migraine.

Without being bound to a particular mechanism, a potential mechanism of action for the role of eIF4E in migraine is presented in FIG. 1. Circled reference numerals in FIG. 1 correspond to the steps as follows.

In step 1, in its inactive state, eIF4E activity is suppressed by 4E-binding protein (4E-BP). Activation of several membrane receptors stimulates mTOR activity, which directly phosphorylates 4E-BP, causing it to dissociate from eIF4E, making it freely available to bind to eIF4G and eIF4A.

In step 2, activation of receptors also stimulates MAPK/ERK activity, which directly phosphorylates MNK. In turn, MNK directly phosphorylates the Serine209 site of eIF4E, causing eIF4E to bind to eIF4G and eIF4A, creating the eIF4F complex. In order to form the eIF4F complex, both 4E-BP and the Ser209 site of eIF4E must be phosphorylated. eFT508 and cercosporamide are drugs that inhibit MNK activity, thus, preventing phosphorylation of eIF4E and, consequently, inhibiting activity-dependent translation. Additionally, 4EGI-1 is a compound that mimics the activity of 4E-BP and can be used to interrupt the binding of eIF4E to eIF4G. These compounds may, therefore, be used to treat, prevent, or inhibit migraine as disclosed herein.

In step 3, binding of eIF4E to eIF4G and eIF4A effectively forms the eIF4E complex, which then recruits the eIF2 pre-initiation complex to the mRNA. The pre-initiation complex consists of a transfer RNA (IRNA) and a small ribosomal subunit, both of which are necessary to translate mRNA.

In step 4, upon recognizing the 5' CAP structure of an mRNA, eIF4E binds to the CAP and stabilizes the eIF4F and pre-initiation complexes, allowing the pre-initiation complex to scan the mRNA for a start codon. Once a start codon is recognized, the eIF2 and eIF4E complexes dissociate, allowing the large ribosomal subunit to bind to the small ribosomal subunit to form the ribosomal initiation complex, which proceeds to the elongation step 5.

In step 5, the ribosomal complex works to translate the mRNA into protein until it reaches a stop codon, in which it becomes unbound and dissociates from the mRNA.

5. Pharmaceutical Formulations and Routes of Administration

Pharmaceuticals may include therapeutic compounds that preventing phosphorylation of Ser209 of eIF4E by suppressing or inhibiting MNK activity.

A. MNK Inhibitors

The MNK inhibitor eFT508 may be used in the therapeutic and other methods described herein. eFT508, also call Tomivosertib, is a potent, highly selective, and orally bioavailable MNK1 and MNK2 inhibitor, with IC50s of 1-2 nM against both isoforms. Its structure is shown below:

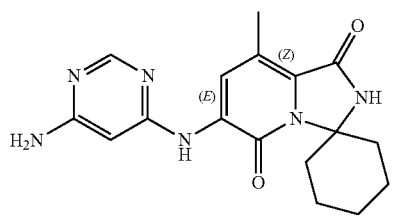

(I)

In vitro, eFT508 reduces eIF4E phosphorylation dose-dependently at serine 209 (IC50=2-16 nM) in tumor cell lines. eFT508 has shown anti-proliferative activity against multiple DLBCL cell lines. Sensitivity to eFT508 in TMD8, OCI-Ly3 and HBL1 DLBCL cell lines is associated with dose-dependent decreases in production of pro-inflammatory cytokines including TNFa, IL-6, IL-10 and CXCL10. eFT508's mechanism of action appears to be decreased TNFa production correlateing with a 2-fold decrease in TNFa mRNA half-life. In vivo, eFT508 shows significant anti-tumor activity in multiple models, both of which harbor activating MyD88 mutations. eFT508 also combines effectively with components of R-CHOP and with novel targeted agents, including ibrutinib and venetoclax, in human lymphoma models.

PCT Application Publication No. WO2017117052 describes methods of assessing whether a human subject having a hyperproliferative disease is likely to respond to treatment with a MNK inhibitor or of identifying a human subject as a candidate for treating a hyperproliferative disease with a MNK inhibitor, as well as methods of treating such disease. WO2018218038 describes compositions and methods for cellular immunotherapy by, for example, generating modified antigen-specific T cells for use with MNK-specific inhibition, as well as methods for generating or increasing central memory, antigen-specific T cells, improving cytotoxic T lymphocyte (CTL) activity of such T cells, or both by MNK-specific inhibition. Both applications describe eFT508 in further detail, and the relevant disclosures from each are incorporated herein by reference with respect to that molecule.

B. Cercosporamide

Cercosporamide is a natural antifungal phytotoxin isolated from the Cercosporidium fungus, which infects the leaves of cassava plants (52). Its antifungal effect results from its selective and potent inhibition of fungal PKC-like 1 kinases (Pkc1), which are central to cell wall integrity (IC50=25 nM for Candida Pkc1) (53). Cercosporamide less effectively inhibits human PKC isoforms PKCα, β, and γ (IC50s=1.02, 0.35, and 5.8 μM, respectively), an action linked to lowering of plasma glucose in hyperglycemic mice (53, 54). However, it potently inhibits MAPK-interacting kinases Mnk1 and Mnk2 (IC50=115 and 11 nM, respectively), reducing protein translation in cancer cells (55, 56). Cercosporamide is orally bioavailable. Cercosporamide has the following structure:

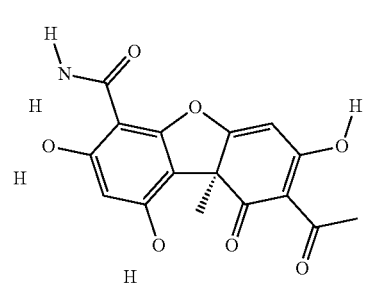

(II)

C. 4EGI-1

4EGI-1 is an inhibitor of eIF4E:eIF4G interaction and prevents eIF4E binding to eIF4G. 4EGI-1 binds eIF4E and inhibits cap-dependent translation but not initiation factor-independent translation (57, 58). 4EGI-1 exhibits activity against Jurkat and A549 cells. 4EGI-1 has the following structure:

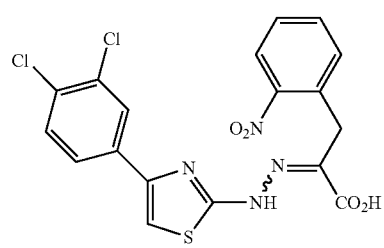

(III)

D. Other Therapeutics

Migraine may also be treated, prevented, or inhibited by administering (i) a therapeutic compound that effectively suppresses or inhibits translation of at least one eIF4E-dependent mRNA, (ii) a therapeutic compound that effectively suppresses or inhibits eIF4E activity, for example by preventing phosphorylation of 4E-BP or Ser209 of eIF4E, or (iii) a therapeutic compound that effectively imitates 4E-BP.

E. Formulations and Routes

Where clinical applications in treating pain are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present disclosure comprise an effective amount of the agent to cells, dissolved or dispersed in a pharmaceutically acceptable carrier or aqueous medium. Such compositions also are referred to as inocula.

The phrase "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include intravenous, oral, nasal, buccal, rectal, vaginal or topical route. Alternatively, administration may be by orthotopic, transdermal, intradermal, subcutaneous, intramuscular, intraperitoneal, intrathecal or intravenous injection. Such compositions would normally be administered as pharmaceutically acceptable compositions, described supra. Of particular interest is transdermal, intraperitoneal, intravenous, subcutaneous or oral administration.

With regard to transdermal delivery, a patch is particularly contemplated. There are five main types of transdermal patches. In the Single-layer Drug-in-Adhesive, the adhesive layer of this system also contains the drug. In this type of patch, the adhesive layer not only serves to adhere the various layers together, along with the entire system to the skin, but is also responsible for the releasing of the drug. The adhesive layer is surrounded by a temporary liner and a backing. In Multi-layer Drug-in-Adhesive, the multi-layer drug-in adhesive patch is similar to the single-layer system in that both adhesive layers are also responsible for the releasing of the drug. One of the layers is for immediate release of the drug and other layer is for control release of drug from the reservoir. The multi-layer system is different however that it adds another layer of drug-in-adhesive, usually separated by a membrane (but not in all cases). This patch also has a temporary liner-layer and a permanent backing.

Unlike the Single layer and Multi-layer Drug-in-adhesive systems, the reservoir transdermal system has a separate drug layer. The drug layer is a liquid compartment containing a drug solution or suspension separated by the adhesive layer. This patch is also backed by the backing layer. In this type of system, the rate of release is zero order. The Matrix system has a drug layer of a semisolid matrix containing a drug solution or suspension. The adhesive layer in this patch surrounds the drug layer partially overlaying it. This is also known as a monolithic device. In Vapor Patches, the adhesive layer not only serves to adhere the various layers together but also to release vapor. The vapor patches are new on the market and they release essential oils for up to 6 hours. Vapor patches release essential oils and are used in cases of decongestion mainly. Other vapor patches on the market are controller vapor patches that improve the quality of sleep. Vapor patches that reduce the quantity of cigarettes that one smokes in a month are also available on the market.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

F. Subjects

The methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice, provided that the species exhibit symptoms of migraine.

G. Therapies i. Monotherapies eFT508, cercosporamide, 4EGI-1, a therapeutic compound that effectively suppresses or inhibits translation of at least one eIF4E-dependent mRNA, a therapeutic compound that effectively suppresses or inhibits eIF4E activity, for example by preventing phosphorylation of 4E-BP or Ser209 of eIF4E, or a therapeutic compound that effectively imitates 4E-BP may be used to treat, prevent, or inhibit migraine.

Treating, preventing, or inhibiting migraine may include preventing the development of all migraine symptoms in a subject who has previously experienced migraine, preventing the development of at least one migraine symptom in a subject who has previously experienced that migraine symptom when the subject is currently experiencing other migraine symptoms, decreasing the duration of at least one migraine symptom in a patient currently experiencing migraine, where the duration is compared to the average duration of the migraine symptom for that subject in prior migraines or the average duration of the migraine symptom in subjects of the same sex and similar age, or decreasing the severity of at least one migraine symptom in a patient currently experiencing migraine, where the severity is compared to the average severity of the migraine symptom for the subject in prior migraines or the average severity of the migraine symptom in subjects of the same sex and similar age.

Migraine symptoms include symptoms experienced during prodrome, aura, attack, and post-drome. Prodrome occurs one or two days before a migraine attack and may include the following symptoms: constipation, mood changes, from depression to euphoria, food cravings, neck stiffness, increased urination, fluid retention, or frequent yawning. Aura may occur before or during a migraine attack and may include the following symptoms: visual phenomena, such as seeing various shapes, bright spots or flashes of light, vision loss, pins and needles sensations in an arm or leg, weakness or numbness in the face or one side of the body, or difficulty speaking. A migraine attack, untreated, typically lasted between 4 and 72 hours and may include the following symptoms: pain usually on one side of the head, but often on both sides, head pain that throbs or pulses, sensitivity to light, sound, smell, or touch, nausea, or vomiting. Post-drome occurs after migraine attack and may include the following symptoms: feeling drained, confused, or washed out for up to a day, feeling elated, or experiencing brief head pain after sudden head movement.

ii. Combination Therapies

All monotherapies disclosed above may be used in any combinations with one another to treat, prevent, or inhibit migraine. Any monotherapies disclosed above may also be used with at least one additional migraine therapeutic. The additional therapeutic may include an acute migraine therapeutic or a therapeutic administered regularly to prevent the onset of migraine in frequent migraine sufferers.

The therapeutics would be provided in a combined amount effective to reduce pain. This process may involve contacting the patient with the therapeutics at the same time. This may be achieved by contacting the patient with a single composition or pharmacological formulation that includes both therapeutics, or by contacting the patient with two distinct compositions or formulations, at the same time, wherein one composition includes a therapeutic as disclosed herein and the other includes the second therapeutic, which may also be a therapeutic as disclosed herein or another migraine therapeutic.

Alternatively, the treatment according to the present disclosure may precede or follow the other treatment by intervals ranging from minutes to weeks. In embodiments where the second therapeutic and the therapeutic as disclosed herein are applied separately to the subject, one would generally ensure that a significant period of time did not expire between each delivery, such that the therapies would still be able to exert an advantageously combined effect on the subject. In such instances, it is contemplated that one would administer both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the therapeutic disclosed herein or the second therapeutic will be desired. Various combinations may be employed, where the therapeutic disclosed herein is "A," and the second therapeutic is "B," as exemplified below:

A/B/A B/A/B B/B/A A/A/B B/A/A A/B/B B/B/B/A B/B/A/B A/A/B/B
A/B/A/B A/B/B/A B/B/A/A B/A/B/A B/A/A/B B/B/B/A A/A/A/B
B/A/A/A A/B/A/A A/A/B/A A/B/B/B B/A/B/B B/B/A/B

Other combinations, including chronic and continuous dosing of one or both agents, are contemplated. Exemplary but non-limiting examples of suitable therapeutics for combination with the compositions and methods of the present disclosure are set out below.

The following is a non-limiting list of migraine therapeutics that may be used in combination with therapeutics of the present disclosure: a CGRP inhibitor, such as Erenumab (Aimovig), fremanezumab (Ajovy), galcanezumab (Emgality), Epitenezumab (Vyepti); a gepant, such as Ubrogepant (Ubrelvy) or Rimegepant (Nurtec); a ditan, such as Lasmiditan (Reyvow); a triptan, such as Sumatriptan, naratriptan, zolmitriptan, rizatriptan, almotriptan, eletriptan, or frovatriptan; an ergotamine, such as Dihydroergotamine; another ergot derivative; and ergotamine or ergot derivative-caffeine combination; an antiemetic, such as Chlorpromazine, Prochlorperazine, or Metoclopramide; a NSAID or non-narcotic analgesic, such as Ketorolac, aspirin, naproxen, diclofenac, ibuprofen, acetaminophen, aspirin, caffeine, Butalbital, ASA, Isometheptene mucate, or dichloralphenazone; an opiate analgesic, such as Butorphanol, codeine, hydrocodone, hydromorphone, or fentanyl citrate; a nonopoate analgesic, such as Tramadol or Tizanidine; a steroid, such as Methylprednisolone or dexamethasone; Lidocaine; Valproic acid; or Propofol.

EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure. In particular, features of the specific embodiments in these examples, alone or in the combinations disclosed in the examples, may be combined with other elements disclosed in the specification. In addition, variations of the specific embodiments in these examples that lack one or more features of the specific example, such as a particular dosage amount or regimen or non-therapeutic aspects of the specific example, are also contemplated by this disclosure.

Example 1—Evaluation of the Role of Protein Synthesis in Migraine

Overview

Mice received a dural injection of interleukin-6 in the absence or presence of the protein synthesis inhibitor anisomycin or the translation initiation inhibitor 4EGI-1 and were tested for facial hypersensitivity. Upon returning to baseline, mice were given a second, non-noxious dural injection of pH 7.0 to test for priming. Additionally, eIF4ES209A mice lacking phosphorylation of mRNA cap-binding protein eIF4E received dural interleukin-6 or were subjected to repeated restraint stress and then tested for facial hypersensitivity. After returning to baseline, mice were given either dural pH 7.0 or a systemic sub-threshold dose of the nitric oxide donor sodium nitroprusside and tested for priming.

Dural injection of interleukin-6 in the presence of anisomycin or 4EGI-1 or in eIF4ES209A mice resulted in the partial attenuation of acute facial hypersensitivity and complete block of hyperalgesic priming. Additionally, hyperalgesic priming following repeated restraint stress was blocked in eIF4ES209A mice.

These examples show that de novo protein synthesis regulated by activity-dependent translation is critical to the development of priming in two preclinical models of migraine. This suggests that targeting the regulation of protein synthesis may be a novel approach for new migraine treatment strategies.

Priming Induced by Dural IL-6 is Blocked by General Protein Synthesis Inhibition Dural IL-6 is able to sensitize mice to cutaneous mechanical stimulation following a sub-threshold stimulus in a model of hyperalgesic priming (13). Given recent data supporting a role for general protein synthesis in the development of hyperalgesia via DRG and spinal pathways (28, 29), and given the potential greater dependence on translation regulation signaling for sensitization in TG versus DRG neurons (30) the hypothesis that protein synthesis is necessary for facial sensitization in this dural stimulation priming model was tested.

Figure 2:
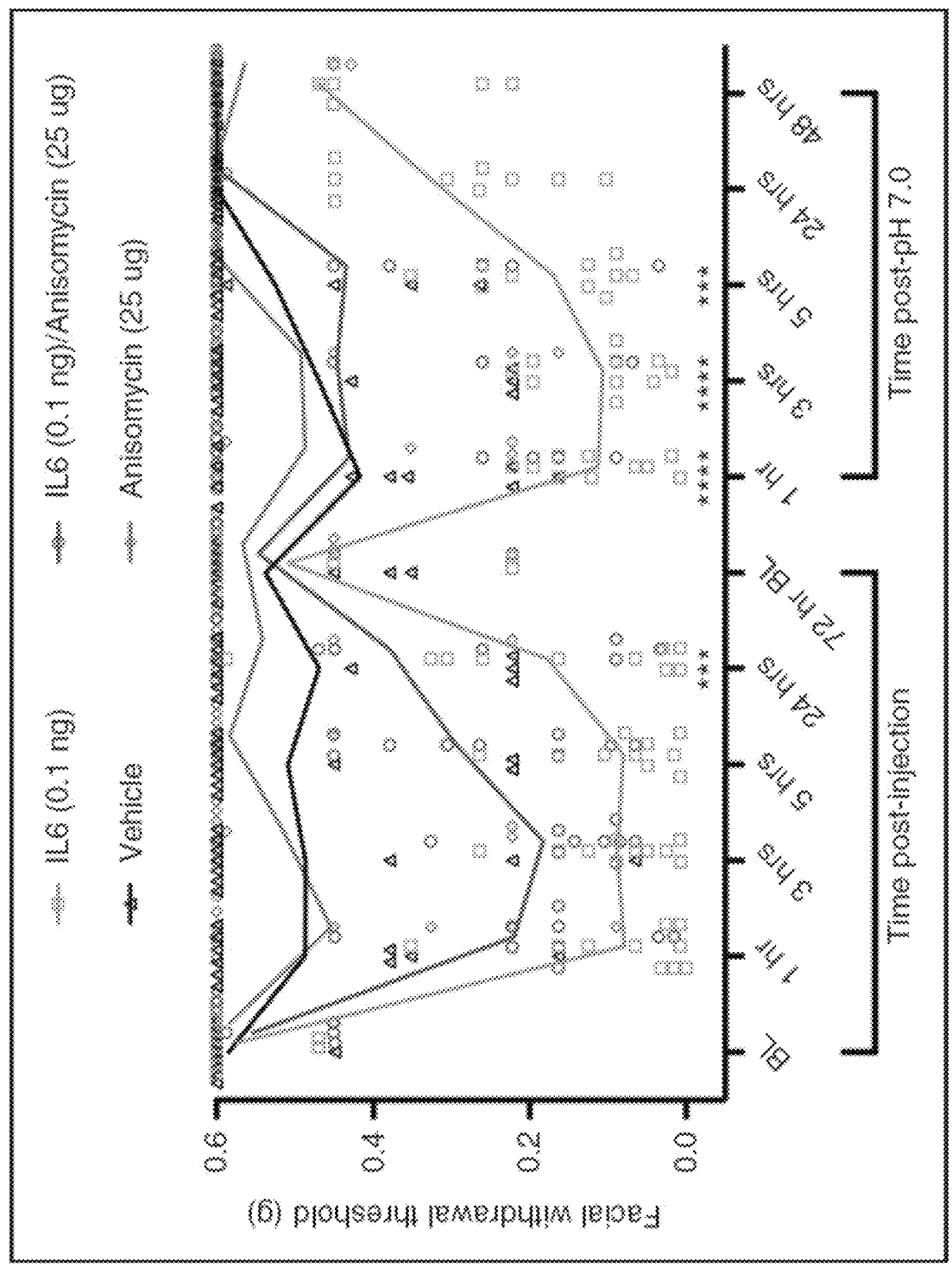
FIG. 2 shows results related to inhibiting cap-dependent translation and long-lasting facial hypersensitivity. The graph shows the facial withdrawal threshold effects of dural co-injection of IL-6 with the general protein synthesis inhibitor anisomycin on hyperalgesic priming to dural pH 7.0 in female ICR mice (n=10 for all groups). Analysis of groups was performed using two-way ANOVA followed by Bonferroni posthoc test (see Table 1 for F-values). *$p<0.05$, $p<0.01$, *$p<0.001$, ****$p<0.0001$.

First female mice were administered either 0.1 ng of IL-6, 25 µg of anisomycin (a general protein synthesis inhibitor), or a co-injection of both onto the dura to induce mechanical facial allodynia that persisted for more than 24 h and resolved by 72 h (FIG. 2). Upon returning to baseline, a second stimulus, SIF (pH 7.0), was administered onto the dura to reveal the presence of hyperalgesic priming from the initial IL-6 stimulus. Although there were only minor differences in acute mechanical hypersensitivity, mice that were initially administered only IL-6 exhibited robust facial hypersensitivity when exposed to low pH. This hypersensitivity persisted for more than 5 h. Conversely, mice that received a co-injection of both IL-6 and anisomycin did not respond to the low pH, suggesting that general protein synthesis is required for the generation of a primed state in mice.

Inhibiting Cap-Dependent Translation Prevents Long-Lasting Facial Hypersensitivity Previous reports have demonstrated that cap-dependent translation induced by IL-6 is dependent on the binding of eIF4E/eIF4G to induce eIF4F complex formation and interruption of this binding via stabilizing 4E-BP1 to eIF4E prevents the priming induced by pronociceptive mediators (27). Translation control by 4E-BP1 has been shown to regulate mechanical hypersensitivity and genetic loss of 4E-BP1 increases excitatory synaptic transmission in the spinal cord, thereby enhancing mechanical nociception (31). To gain a better understanding of the molecular mechanisms underlying the priming induced by IL-6, a similar approach was used to investigate the role of eIF4E phosphorylation and subsequent cap-dependent translation.

Figure 3:
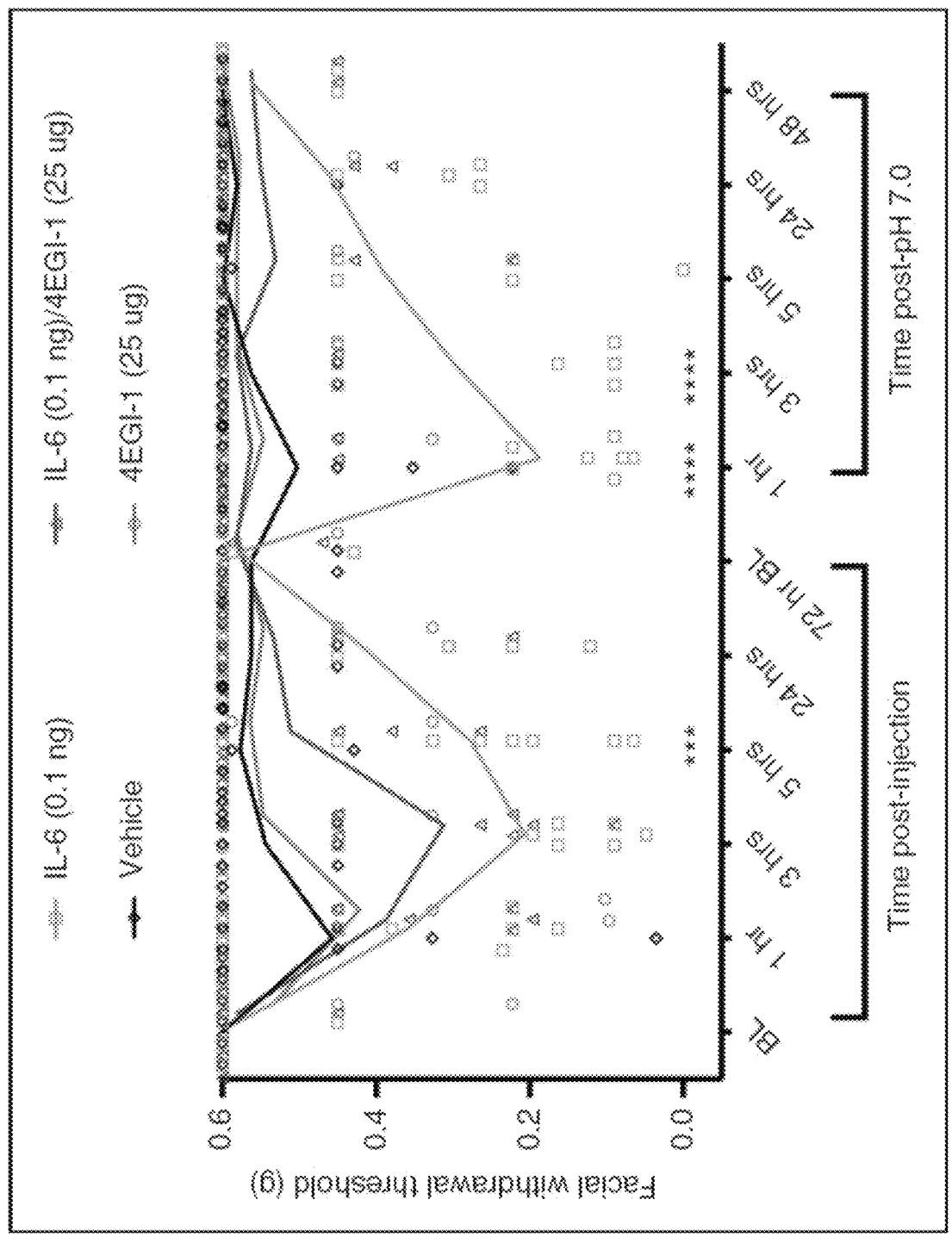
FIG. 3 shows results related to the role of eIF4E phosphorylation in priming following repeated stress. The graph shows the facial withdrawal threshold effects of IL-6-induced priming to pH 7.0 after co-treatment with 4EGI-1 in female ICR mice (n=8 for all groups). Analysis of groups was performed using two-way ANOVA followed by Bonferroni post-hoc test (see Table 1 for F-values). *$p<0.05$, $p<0.01$, *$p<0.001$, ****$p<0.0001$.

Similar to the experiments used to generate FIG. 2, 0.1 ng of IL-6, 25 µg of 4EGI-1, a compound that mimics the activity of 4E-BP1, or a co-injection of both was administered onto the dura of female mice (FIG. 3). The resulting mechanical allodynia induced by IL-6 persisted for more than 24 h and resolved after 72 h. Upon returning to baseline, mice were exposed to a dural injection of low pH. Mice previously treated with IL-6 alone demonstrated cutaneous mechanical hypersensitivity. As with anisomycin, acute facial hypersensitivity was partially attenuated and the response to low pH was robustly blocked in mice that received a co-injection of IL-6 and 4EGI-1. Thus, assembly of the eIF4F complex locally in the dura appears to be critical to the development of long-lasting mechanical hypersensitivity following repeated stress.

eIF4E Phosphorylation is Necessary for Priming Following Repeated Stress

Figure 4A:
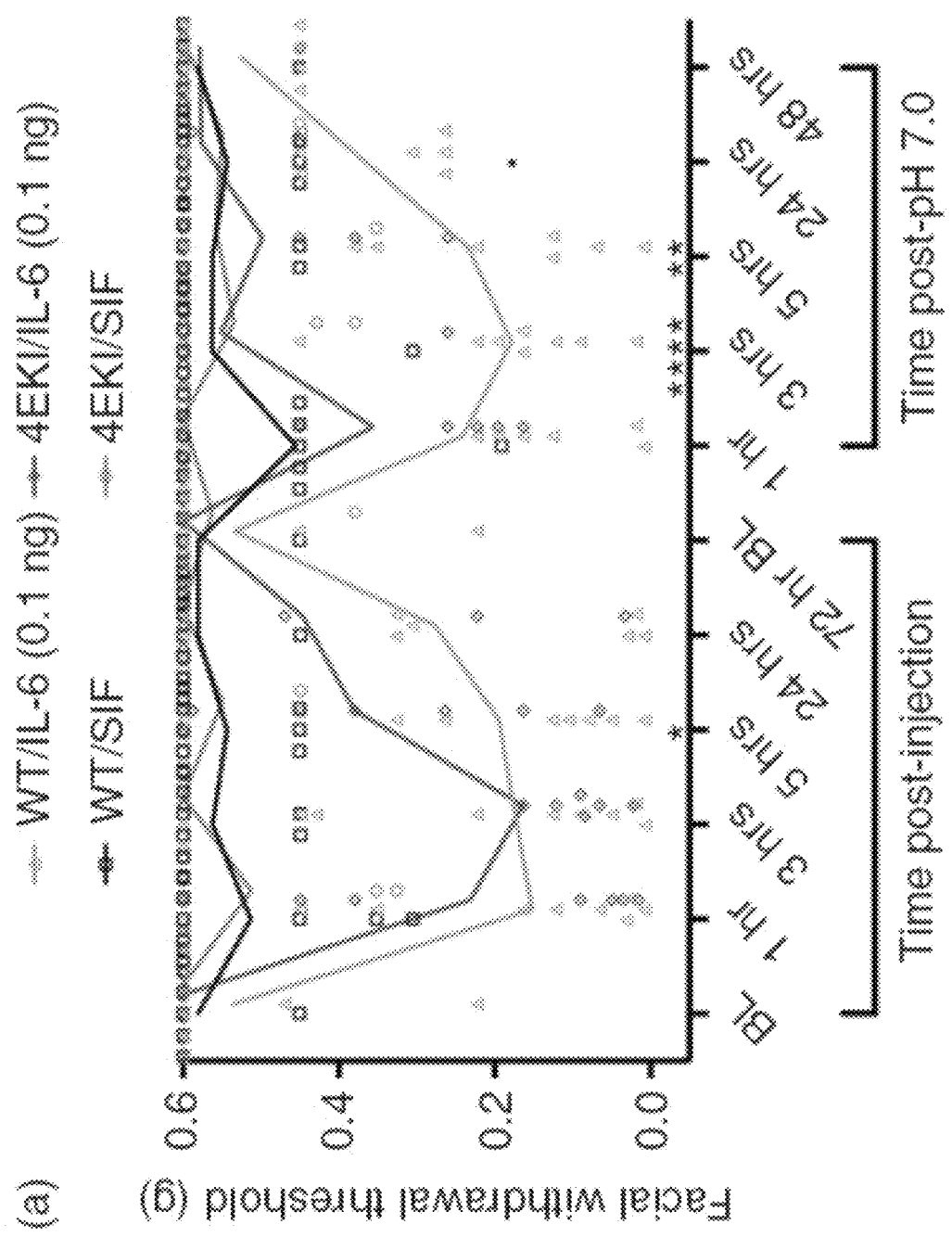
FIGS. 4A-4B show results related to the role of eIF4E phosphorylation in priming in eIF4E$^{S209A}$ mice. The graphs show facial withdrawal threshold effects in female (FIG. 4A)
Figure 4B:
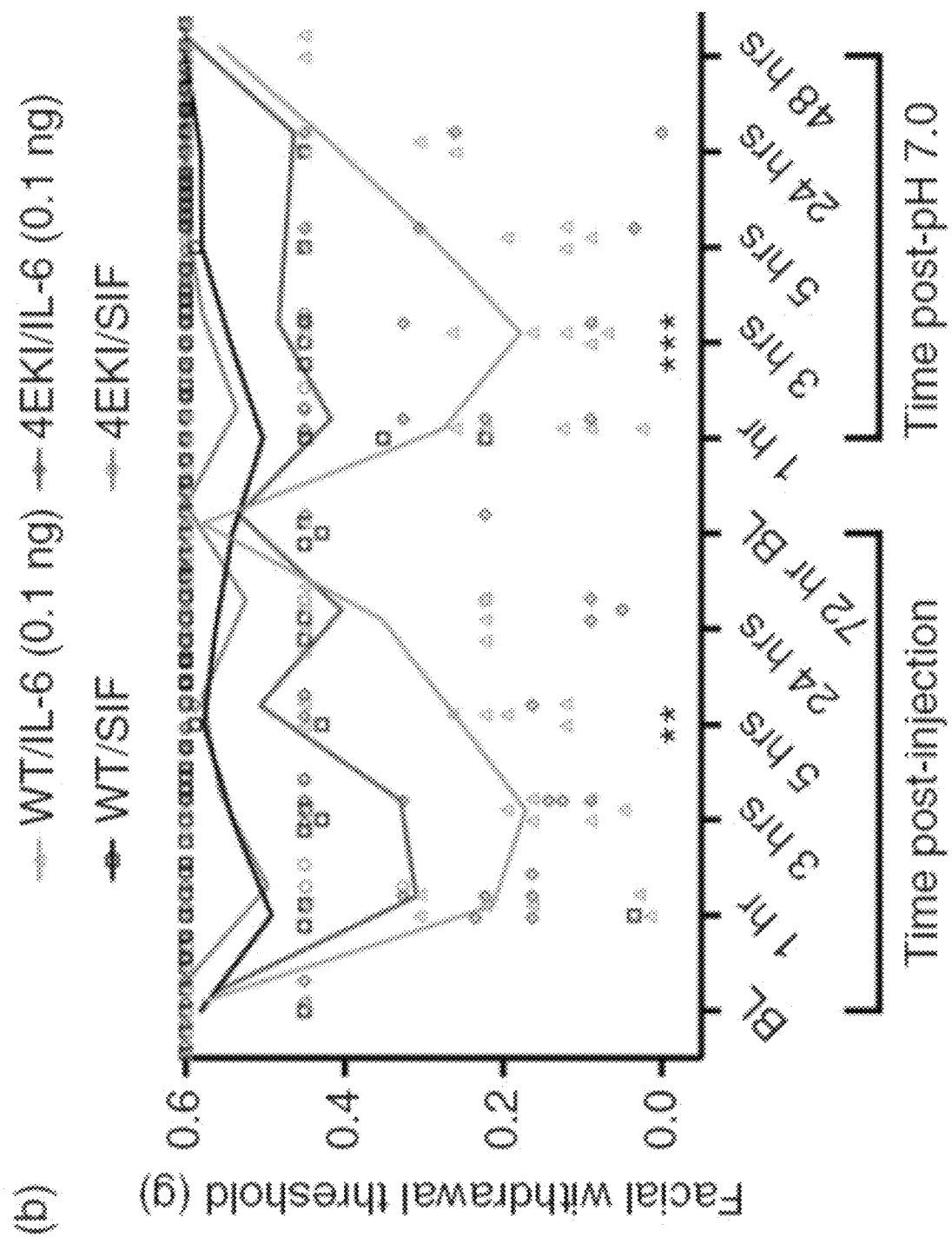

Previous studies have shown that eIF4E$^{S209A}$ mice, which lack phosphorylation of eIF4E at Ser209, exhibit reduced nociceptor sensitization and hyperalgesic priming in response to pronociceptive and inflammatory factors, including NGF and IL-6 (24, 32). To test the hypothesis that eIF4E phosphorylation is important for priming following dural stimulation or repeated stress, these same eIF4ES209A were used for testing in mouse migraine models. As described above, IL-6 was administered onto the dura of female and male eIF4ES209A mice, followed by dural pH 7.0 (FIGS. 4A-B). Unlike WT mice, acute mechanical hypersensitivity was partially attenuated and priming to dural pH 7.0 was blocked in both sexes of eIF4E$^{S209A}$ mice, showing that eIF4E phosphorylation is critical to establishing long-lasting hypersensitivity induced by dural IL-6.

Mice exposed to repeated restraint stress become primed to subthreshold doses of the nitric oxide-donor sodium nitroprusside (SNP). Stress is the number one reported trigger of migraine among humans (33) and NO donors are among the most reliable experimental triggers of migraine attacks (34, 35). Accordingly, both WT and eIF4ES209A mice were subjected to repeated restraint stress. Following their return to baseline nociceptive thresholds, a 0.1 mg/kg IP injection of SNP was administered (FIGS. 5A-B). Priming to SNP was completely blocked in stressed eIF4E$^{S209A}$ mice compared to a robust increase in mechanical hypersensitivity in stressed WT mice. This identifies a key role for eIF4E phosphorylation in the transition from acute to long-lasting hypersensitivity and suggests eIF4E phosphorylation as a potential mechanism underlying neuronal plasticity in migraine.

Phosphorylation of eIF4E is Differentially Regulated After Repeated Restraint Stress To determine the time points at which eIF4E phosphorylation is altered in the stress paradigm, protein lysates from the dura and TG of WT C57BL/6 mice obtained at multiple time points after day 3 of the stress protocol were examined (FIGS. 6A-B). An almost 50% increase in the expression level of p-eIF4E was seen in the TG 1 h after day 3 of stress, an effect that was diminished by 3 h. In the dura, the effects were completely opposite, with an almost 50% decrease in p-eIF4E expression levels 1 h after stress, but an increase of over 75% in expression levels by 3 h. Phosphorylation levels of eIF4E were decreased 24 h after day 3 of stress in both tissues. This indicates that eIF4E phosphorylation-mediated events occur earlier in the TG than they do in the dura in response to stress, providing evidence that the temporal components of this key biochemical event are dynamically regulated.

Genetic Inhibition of MNK Partially Attenuates Facial Hypersensitivity and Hyperalgesic Priming Caused by Dural IL-6

In an experimental scheme set forth in FIG. 7A, male and female wild-type (WT) C57/BL6 and MNK1 KO mice (which lack the essential translation-initiating kinase, mitogen-activated protein kinase-interacting kinase 1 [MNK1]) were given a 5 μL injection of the pro-inflammatory cytokine interleukin-6 (IL-6) (0.1 ng) and tested for facial mechanical hypersensitivity and grimacing. 72 hours following dural IL-6, mice returned to baseline nociceptive thresholds, upon which they were administered a second 5 μL dural injection of synthetic interstitial fluid (SIF) solution (pH=7) to check for the presence of hyperalgesic priming. Control mice received dural SIF at physiological pH. Dural IL-6 induced acute periorbital hypersensitivity and hyperalgesic priming to dural pH 7.0 in WT mice; however, MNK1 KO mice exhibited significantly reduced von Frey thresholds following dural IL-6 and were not primed (FIG. 7B). A similar effect was observed in grimace measurements, in which MNK1 KO mice had significantly lower mean grimace scores (MGS) compared to WT mice following both dural IL-6 and pH 7.0 (FIG. 7C). This indicates that MNK plays a role in phosphorylation of eIF4E in this mouse migraine model.

The MNK/eIF4E Pathway Plays a Role in the Development of Migraine

The susceptibility of migraine patients to attacks following exposure to normally innocuous triggers strongly implicates sensitization of the trigeminovascular system, leading to lower activation thresholds for nociception to occur. Robust changes in gene expression regulated by activity-dependent translation are key to nociceptor plasticity and phenotypic alterations and are thought to underlie neuronal sensitization (29). IL-6-induced phosphorylation of ERK has been shown to modulate the sodium channel Nav1.7, resulting in prolonged migraine-related pain (36) and activation of ERK/MAPK pathways can ultimately lead to changes in transient receptor potential (TRP) channel function, a family of proteins which have been implicated in migraine pathophysiology (37-39). Co-application of dural IL-6 and anisomycin partially attenuated the resulting acute facial hypersensitivity and completely blocked the development of a primed state in mice, suggesting that protein synthesis may be critical for the development of long-lasting mechanical hypersensitivity. The comparable results between local administration of anisomycin and 4EGI-1 suggest that the newly synthesized proteins required to establish priming are regulated by cap-dependent translation. In accordance with this, our results from injecting IL-6 onto the dura of eIF4E$^{S209A}$ mice and MNK1 KO mice suggest that eIF4E phosphorylation by MNK1 is key for long-lasting facial mechanical hypersensitivity. Thus, similar to reports in other preclinical models of pain 24, activity-dependent translation appears to be critical for the sensitization of trigeminal nociceptors by pronociceptive factors.

Headaches can be triggered in migraine patients by a wide range of noxious and innocuous stimuli, making it difficult to parse out which mechanisms may be most relevant for trigeminal activation and sensitization. Since the most common and frequent trigger of migraine is stress (33), use of this trigger is one of the more clinically relevant models for mechanistic investigation. Utilizing a repeated stress model with eIF4E$^{S209A}$ mice showed the role of eIF4E phosphorylation in a much more robust model of hypersensitivity that was not isolated to local cephalic regions, but rather the entire body. In eIF4E$^{S209A}$ mice, the loss of NO-donor induced priming normally observed after stress highlights a critical role for eIF4E phosphorylation in the development of long-lasting mechanical hypersensitivity. Additionally, in WT mice, phosphorylation of eIF4E in the dura and TG was differentially expressed across multiple time points following stress, with an increase in p-eIF4E occurring 1 h after stress in the TG and being downregulated by 3 h while the opposite effect was observed in the dura, indicating that robust changes in eIF4E phosphorylation occur after repeated stress and that a genetic loss of this phosphorylation prevents the development of hyperalgesic priming.

Targeting local translation in DRG sensory axons has been proposed as a potential treatment for many types of inflammatory and neuropathic pain (23); however, whether the translation of mRNAs that contribute to priming of dural afferents occurs locally in meningeal sensory axons or at distal sites in the TG remains unclear. A previous study found that while local co-injection of IL-6 with anisomycin into the hindpaw prevented acute mechanical hypersensitivity, co-injection with a transcription inhibitor had no effect, suggesting that local translation contributing to acute pain in the hindpaw is dependent on pre-existing pools of mRNA (27). Given the similarities between the DRG and TG, it is plausible to suggest that the translation events regulating acute and long-lasting hypersensitivity caused by dural IL-6 are dependent on local pools of mRNA as well; however, one key difference between these studies is that attenuation of dural IL-6-induced facial allodynia begins at later time points in the acute phase. One potential explanation for this can be attributed to the location of testing following injection. For example, other studies tested the hindpaw in the same location that the injection was given; in these examples injection was directly onto the dura, but testing was in the periorbital region of the face. The delay in attenuation of acute hypersensitivity might indicate that nascent protein synthesis in response to dural stimulation occurs some distance away from the initial injection site. Additionally, if these translation events are indeed occurring locally in meningeal sensory axons, then changes in synaptic plasticity in the TG and possibly even the ophthalmic nerve (innervating the periorbital region) may be dynamically and temporally regulated following injection.

Studies have demonstrated robust increases in the expression levels of mRNAs that modulate acid-sensing ion channels (ASICs) (40) and TRP channels (41) in the TNC in response to noxious odors and repeated dural stimulation, respectively. Although it is currently unknown which eIF4E-dependent mRNAs are most critical in these models, eIF4E phosphorylation has been shown to regulate the translation of brain-derived neurotropic factor (BDNF) mRNA in mouse DRG (32). BDNF is a key player in the maintenance of long-term potentiation (LTP) (42-44) and has been implicated in maintaining persistent pain states (45, 46). Additionally, multiple lines of evidence suggest a role for BDNF in headache (47-50). In support of these claims, afferent input from the meninges is capable of producing BDNF-dependent priming of the trigeminovascular system (51). These examples demonstrate that de novo protein synthesis regulated by activity-dependent translation is critical to the development of cutaneous facial hypersensitivity following dural stimulation or repeated stress.

Key Findings

- Local inhibition of de novo protein synthesis prevents the long-lasting facial hypersensitivity that is normally observed following noxious stimulation of the dura mater.
- Persistent facial hypersensitivity induced by noxious stimulation of the dura mater is dependent on the association of eIF4G with eIF4E and subsequent initiation of cap-dependent translation.
- The translational regulation of protein synthesis via eIF4E phosphorylation is critical for the development of a primed state following dural stimulation or repeated stress.
- Phosphorylation of eIF4E is differentially regulated across time points in the dura mater and trigeminal ganglia following repeated restraint stress.

Example 2—Materials and Methods

Experimental Animals

Male and female eIF4ES209A mice on a C57BL/6 background were generated in the Sonenberg laboratory at McGill University as previously described (25) and bred at The University of Texas at Dallas to generate experimental animals. These animals were genotyped using DNA from tail clips taken at the time of weaning and were backcrossed to C57BL/6 background for at least 10 generations before experiments. In experiments involving transgenic mice, the control mice used were wild-type (WT) mice generated in the UT Dallas breeding colony from crossings of heterozygous eIF4E$^{S209A}$ mice with WT C57BL/6 mice (Envigo). Male and female ICR (CD-1) mice were outbred and purchased from Envigo. All behavior experiments were performed using mice aged 6-8 weeks (~25-30 g) at the start of the experiment. All mice were housed on 12 h light/dark cycles with lights on at 7:00 AM. All mice were housed in groups of four animals per cage and had food and water available ad libitum. All behavioral experiments were performed between the hours of 9:00 AM and 5:00 PM. Mice were randomized to groups from multiple cages and investigators were blinded to treatment groups in all experiments. All animal procedures were approved by the Institutional Animal Care and Use Committees at The University of Texas at Dallas and were performed in accordance with the ARRIVE guidelines as well as the policies of the International Association for the Study of Pain and the National Institutes of Health guidelines for animal research.

Drugs and Antibodies

Human recombinant IL-6 protein (R&D Systems) stock solution (100 mg/mL) was prepared in sterile 0.1% BSA and diluted to 1 ng/mL in synthetic interstitial fluid (SIF) consisting of 135 mM NaCl, 5 mM KCl, 10 mM HEPES, 2 mM $CaCl_2$, 10 mM glucose, 1 mM $MgCl_2$ (pH 7.4, 310 mOsm). Anisomycin (Tocris) stock solution (135 mg/mL) and 4EGI-1 (Enzo) stock solution (20 mg/mL) were both prepared in sterile 0.1% BSA and diluted to 5 mg/mL in SIF. Sodium nitroprusside (SNP) (Sigma-Aldrich) was prepared in sterile phosphate buffered saline (PBS) at the time of use and was kept away from light. For dural injections, mice received 5 mL injections of either IL-6, anisomycin, 4EGI-1, SIF, or a combination of IL-6 and anisomycin or IL-6 and 4EGI-1 for acute testing. For testing the ability of mice to prime to the initial stimulus in these dural injection experiments, 5 mL of SIF pH 7.0 were administered onto the dura. In repeated restraint stress experiments, which used SNP to test priming, a subthreshold dose of 0.1 mg/kg of SNP was administered intraperitoneally as a 150 mL injection. For western blotting experiments, p-eIF4E (Cell Signaling #9741S) and total-eIF4E (Cell Signaling #9742S) antibodies were used for primary incubation.

Mouse Dural Injections

Mouse dural injections were performed as previously described (13). Mice were anesthetized under isoflurane for <2 min with <2.5-3% isoflurane via a chamber. While anesthetized, treatments were injected in a volume of 5 mL via a modified internal cannula (Invivo1, part #8IC313ISPCXC, Internal Cannula, standard, 28 gauge, fit to 0.5 mm). The inner projection of the cannula was used to inject through the soft tissue at the intersection of the lambdoidal and sagittal sutures. The length of the projection was adjusted, using calipers, to be from 0.5 to 0.7 mm based on the animal weight (25-30 g) so as to not puncture the dura. Control mice received a 5 mL dural injection of SIF (pH 7.4, 310 mOsm).

Repeated Restraint Stress

Mice were stressed as previously described (26). Mice were placed right-side up into tail vein injection tubes (Stolting #51338) with the nose through the provided breathing hole and the tail through the slotted tail piece. The slotted tail piece was tightened so as to prevent the mouse from rotating in the tube, but loose enough to allow the animal to breathe. Mice were stressed between the hours of 10:00 AM to 12.00 PM for 2 h per day for three consecutive days. Control mice were placed into a separate room and deprived of food and water for the same 2-h interval for three consecutive days.

Von Frey Testing

Mice were conditioned for five continuous minutes by handling, 24 h before habituation. Mice were habituated to paper cups (Choice 4 oz paper cups: 6.5 cm top diameter, 4.5 cm bottom diameter, 72.5 cm length) while in testing chambers for 2 h per day and for at least 2 days before measuring a baseline (13). Each mouse typically used their same assigned paper cup for the remainder of the experiment. Animals were given food while in testing chambers to allow for testing as previously described. Filament thresholds were determined using the Dixon "up-and-down" method. Testing in mice began with 0.07 g on the face and increased in weight to a maximum of 0.6 g on the face. The testing timelines for dural injection experiments and stress experiments were conducted as previously described in (13) and (26), respectively. In both experimental paradigms, once the mice returned to baseline, a sub-threshold dose of compound was administered either onto the dura (pH 7.0) or intraperitoneally (sodium nitroprusside). Mice were then tested for the ability of the initial stimulus to cause priming to the sub-threshold stimulus. All investigators were blinded to experimental conditions.

Western Blotting

Female mice were used for all western blotting experiments and were killed by decapitation following anesthesia with tissues being flash frozen on dry ice. Frozen tissues were homogenized using a pestle in lysis buffer (50 mM Tris, pH 7.4, 150 mM NaCl, 1 mM EDTA, pH 8.0, and 1% Triton X-100) containing protease and phosphatase inhibitors (Sigma-Aldrich) and then sonicated for 10 sec. TG and dura tissues were harvested following 3 days of repeated restraint stress at the time-points provided in the Results section. To clear debris, samples were centrifuged at 14,000 rpm for 15 min at 4° C. 15 mg of protein was loaded into each well and separated by a 10% SDS-PAGE gel. Proteins were transferred to a 0.45 PVDF membrane (Millipore) at 30 V overnight at 4° C. Membranes were then blocked with 5% non-fat dry milk in 1×Tris buffer solution containing Tween 20 (TTBS) for 2 h. Membranes were washed in 1×TTBS three times for 5 min each then incubated with primary antibody overnight at 4° C. The following day, membranes were washed three times in 1×TTBS for 5 min each then incubated with the goat antirabbit secondary antibody (Jackson Immunoresearch) at room temperature for 1 h. Membranes were then washed with 1×TTBS six times for 5 min each. Signals were detected using Immobilon Western Chemiluminescent HRP Substrate (Millipore). Bands were visualized with a Bio-Rad ChemiDoc Touch and over-saturated pixels were excluded from the final analysis. Blots were first probed for phosphorylated eIF4E (peIF4E) (Cell Signaling; 1:3000), then stripped and re-probed for total eIF4E (teIF4E) (Cell Signaling; 1:3000). Equal loading was verified using GAPDH (Cell Signaling; 1:5000) as a control. For quantitative analysis, peIF4E was normalized to teIF4E. Analysis was performed using Image Lab version 6.0.1.

Experimental Design and Statistical Analysis

Only female mice in the dural IL-6 experiments involving ICR mice, due to the higher frequency of migraine among women. The rationale for this was based on pilot studies in which co-injection of dural IL-6 with either anisomycin or 4EGI-1 revealed no sex differences in these animals. Additionally, previously reported findings from our laboratory revealed similar effects in males when IL-6 is co-injected with anisomycin or 4EGI-1 into the hindpaw (27). Since there have been no comparable studies in eIF4E$^{S209A}$ mice or the MNK1 KO mice, both females and males were used to explore the possibility of a sex difference in these genotypes with these stimuli. All behavioral data are represented as individual data points with means (lines). Western blot data are represented as means±SEM.

Behavioral data were analyzed for multiple comparisons at each time point via two-way ANOVA and Bonferroni's post-hoc test. F-values for each analysis are presented in Table 1. Student's unpaired two-tailed t-test was used for individual mean comparisons when appropriate. Data analysis was performed using Prism version 8.3 for Mac OS X. Significance was set at p<0.05 for all analyses. Power analysis was performed using G power for comparison of the means between groups using expected effect sizes based on pilot studies and previously published data in other models (24).

All investigators were blinded to genotype and treatment during testing and scoring. Each experiment was independently replicated twice.

TABLE 1

F-values obtained from two-way ANOVA analysis comparing mean effects within rows are presented for each figure.

| FIG. | Interaction | Row factor | Column factor |
|---|---|---|---|
| 1 | $F_{(30, 385)} = 3.569$ | $F_{(10, 385)} = 17.81$ | $F_{(3, 385)} = 98.19$ |
| 2 | $F_{(30, 308)} = 2.948$ | $F_{(10, 308)} = 9.244$ | $F_{(3, 308)} = 36.81$ |
| 3(a) | $F_{(30, 275)} = 3.402$ | $F_{(10, 275)} = 10.43$ | $F_{(3, 275)} = 66.87$ |
| 3(b) | $F_{(30, 286)} = 2.219$ | $F_{(10, 286)} = 8.967$ | $F_{(3, 286)} = 47.16$ |
| 4(a) | $F_{(24, 189)} = 4.444$ | $F_{(8, 189)} = 14.01$ | $F_{(3, 189)} = 41.06$ |
| 4(b) | $F_{(24, 180)} = 11.43$ | $F_{(8, 180)} = 32.85$ | $F_{(3, 180)} = 80.98$ |

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar 10 substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference:

1. Headache Classification Committee of the International Headache Society. The International Classification of Headache Disorders, 3rd edition (beta version). Cephalalgia 2013; 33: 629-808.
2. Katsarava Z, Manack A, Yoon M S, et al. Chronic migraine: Classification and comparisons. Cephalalgia 2011; 31: 520-529.
3. Bartsch T and Goadsby P J. Increased responses in trigeminocervical nociceptive neurons to cervical input after stimulation of the dura mater. Brain 2003; 126: 1801-1813.
4. Pietrobon D. Migraine: New molecular mechanisms. Neuroscientist 2005; 11: 373-386.
5. Levy D, Burstein R, Kainz V, et al. Mast cell degranulation activates a pain pathway underlying migraine headache. Pain 2007; 130: 166-176.
6. Zhang X C, Strassman A M, Burstein R, et al. Sensitization and activation of intracranial meningeal nociceptors by mast cell mediators. J Pharmacol Exp Ther 2007; 322: 806-812.
7. Wei X, Melemedjian O K, Ahn D D, et al. Dural fibroblasts play a potential role in headache pathophysiology. Pain 2014; 155: 1238-1244.
8. Strassman A M, Raymond S A and Burstein R. Sensitization of meningeal sensory neurons and the origin of headaches. Nature 1996; 384: 560-564.
9. Edvinsson L, Brodin E, Jansen I, et al. Neurokinin A in cerebral vessels: Characterization, localization and effects in vitro. Regul Pept 1988; 20: 181-197.
10. Burstein R, Yamamura H, Malick A, et al. Chemical stimulation of the intracranial dura induces enhanced responses to facial stimulation in brain stem trigeminal neurons. J Neurophysiol 1998; 79: 964-982.
11. Uddman R and Edvinsson L. Neuropeptides in the cerebral circulation. Cerebrovasc Brain Metab Rev 1989; 1:230-252.
12. Ebersberger A, Averbeck B, Messlinger K, et al. Release of substance P, calcitonin gene-related peptide and prostaglandin E2 from rat dura mater encephali following electrical and chemical stimulation in vitro. Neuroscience 1999; 89: 901-907.
13. Burgos-Vega C C, Quigley L D, Trevisan Dos Santos G, et al. Non-invasive dural stimulation in mice: A novel preclinical model of migraine. Cephalalgia 2019; 39: 123-134.
14. Ji R R and Woolf C J. Neuronal plasticity and signal transduction in nociceptive neurons: implications for the initiation and maintenance of pathological pain. Neurobiol Dis 2001; 8: 1-10.
15. Reichling D B and Levine J D. Critical role of nociceptor plasticity in chronic pain. Trends Neurosci 2009; 32: 611-618.
16. Sandkuhler J. Understanding LTP in pain pathways. Mol Pain 2007; 3: 9.
17. Price T J and Geranton S M. Translating nociceptor sensitivity: The role of axonal protein synthesis in nociceptor physiology. Eur J Neurosci 2009; 29: 2253-2263.
18. Price T J and Dussor G. AMPK: An emerging target for modification of injury-induced pain plasticity. Neurosci Lett 2013; 557: 9-18.
19. Woolf C J and Costigan M. Transcriptional and posttranslational plasticity and the generation of inflammatory pain. Proc Natl Acad Sci USA 1999; 96: 7723-7730.
20. Martin K C, Barad M and Kandel E R. Local protein synthesis and its role in synapse-specific plasticity. Curr Opin Neurobiol 2000; 10: 587-592.
21. Klann E, Antion M D, Banko J L, et al. Synaptic plasticity and translation initiation. Learn Mem 2004; 11: 365-372.
22. Price T J. Translation regulation and pain special issue editorial for neurobiology of pain. Neurobiol Pain 2018; 4: 1.
23. Asiedu M N, Dussor G and Price T J. Targeting AMPK for the alleviation of pathological pain. Exp Suppl 2016; 107: 257-285.
24. Moy J K, Khoutorsky A, Asiedu M N, et al. The MNKeIF4E signaling axis contributes to injury-induced nociceptive plasticity and the dDevelopment of chronic pain. J Neurosci 2017; 37: 7481-7499.
25. Furic L, Rong L, Larsson O, et al. eIF4E phosphorylation promotes tumorigenesis and is associated with prostate cancer progression. Proc Natl Acad Sci USA 2010; 107: 14134-14139.
26. Avona A, Mason B N, Lackovic J, et al. Repetitive stress in mice causes migraine-like behaviors and CGRPdependent hyperalgesic priming to a migraine trigger. Pain 2020; 161: 2539-2550.
27. Melemedjian O K, Asiedu M N, Tillu D V, et al. IL-6 -and NGF-induced rapid control of protein synthesis and nociceptive plasticity via convergent signaling to the eIF4F complex. J Neurosci 2010; 30: 15113-15123.
28. Bonin R P and De Koninck Y. A spinal analog of memory reconsolidation enables reversal of hyperalgesia. Nat Neurosci 2014; 17: 1043-1045.
29. Khoutorsky A and Price T J. Translational control mechanisms in persistent pain. Trends Neurosci 2018; 41: 100-114.
30. Megat S, Ray P R, Tavares-Ferreira D, et al. Differences between dorsal root and trigeminal ganglion nociceptors in mice revealed by translational profiling. J Neurosci 2019; 39: 6829-6847.
31. Khoutorsky A, Bonin R P, Sorge R E, et al. Translational control of nociception via 4E-binding protein 1. Elife 2015; 4: e12002.
32. Moy J K, Khoutorsky A, Asiedu M N, et al. eIF4E phosphorylation influences Bdnf mRNA translation in mouse dorsal root ganglion neurons. Front Cell Neurosci 2018; 12: 29.
33. Kelman L. The triggers or precipitants of the acute migraine attack. Cephalalgia 2007; 27: 394-402.
34. Olesen J and Jansen-Olesen I. Nitric oxide mechanisms in migraine. Pathol Biol (Paris) 2000; 48: 648-657.
35. Olesen J. The role of nitric oxide (NO) in migraine, tension-type headache and cluster headache. Pharmacol Ther 2008; 120: 157-171.
36. Yan J, Melemedjian O K, Price T J, et al. Sensitization of dural afferents underlies migraine-related behavior following meningeal application of interleukin-6 (IL-6). Mol Pain 2012; 8: 6.
37. Wei X, Edelmayer R M, Yan J, et al. Activation of TRPV4 on dural afferents produces headache-related behavior in a preclinical rat model. Cephalalgia 2011; 31: 1595-1600.
38. Benemei S and Dussor G. TRP channels and migraine: Recent developments and new therapeutic opportunities. Pharmaceuticals (Basel) 2019; 12: 54.
39. Dussor G, Yan J, Xie J Y, et al. Targeting TRP channels for novel migraine therapeutics. ACS Chem Neurosci 2014; 5: 1085-1096.

40. Zhang L, Kunkler P E, Knopp K L, et al. Role of intraganglionic transmission in the trigeminovascular pathway. Mol Pain 2019; 15: 1744806919836570.
41. Zhou H, Wang X, Wang S, et al. Inhibition of nerve growth factor signaling alleviates repeated dural stimulation-induced hyperalgesia in rats. Neuroscience 2019; 398: 252-262.
42. Kerr B J, Bradbury E J, Bennett D L, et al. Brain-derived neurotrophic factor modulates nociceptive sensory inputs and NMDA-evoked responses in the rat spinal cord. J Neurosci 1999; 19: 5138-5148. 1999 Jun. 15.
43. Lu Y, Christian K and Lu B. BDNF: A key regulator for protein synthesis-dependent LTP and long-term memory? Neurobiol Learn Mem 2008; 89: 312-323.
44. Zhou L J, Zhong Y, Ren W J, et al. BDNF induces late-phase LTP of C-fiber evoked field potentials in rat spinal dorsal horn. Exp Neurol 2008; 212: 507-514.
45. Melemedjian O K, Tillu D V, Asiedu M N, et al. BDNF regulates atypical PKC at spinal synapses to initiate and maintain a centralized chronic pain state. Mol Pain 2013; 9: 12.
46. Matayoshi S, Jiang N, Katafuchi T, et al. Actions of brain-derived neurotrophic factor on spinal nociceptive transmission during inflammation in the rat. J Physiol 2005; 569: 685-695.
47. Blandini F, Rinaldi L, Tassorelli C, et al. Peripheral levels of BDNF and NGF in primary headaches. Cephalalgia 2006; 26: 136-142.
48. Fischer M, Wille G, Klien S, et al. Brain-derived neurotrophic factor in primary headaches. J Headache Pain 2012; 13: 469-475.
49. Tanure M T, Gomez R S, Hurtado R C, et al. Increased serum levels of brain-derived neurotropic factor during migraine attacks: A pilot study. J Headache Pain 2010; 11: 427-430.
50. Buldyrev I, Tanner N M, Hsieh H Y, et al. Calcitonin gene-related peptide enhances release of native brain-derived neurotrophic factor from trigeminal ganglion neurons. J Neurochem 2006; 99: 1338-1350.
51. Burgos-Vega C C, Quigley L D, Avona A, et al. Dural stimulation in rats causes brain-derived neurotrophic factor-dependent priming to subthreshold stimuli including a migraine trigger. Pain 2016; 157: 2722-2730.
52. Sugawara, F., Strobel, S., Strobel, G., et al. The structure and biological activity of cercosporamide from Cercosporidium henningsii. J. Org. Chem. 56, 909-910 (1991).
53. Sussman, A., Huss, K., Chio, L. C., et al. Discovery of cercosporamide, a known antifungal natural product, as a selective Pkc1 kinase inhibitor through high-throughput screening. Eukaryot.Cell 3(4), 932-943 (2004).
54. Furukawa, A., Arita, T., Satoh. S., et al. (—)-Cercosporamide derivatives as novel antihyperglycemic agents. Bioorganic & Medicinal Chemistry Letters 19(3), 724-726 (2009).
55. Konicek, B. W., Stephens, J. R., McNulty, A. M., et al. Therapeutic inhibition of MAP kinase interacting kinase blocks eukaryotic initiation factor 4E phosphorylation and suppresses outgrowth of experimental lung metastases. Cancer Research 71(5), 1849-1857 (2011).
56. Hou, J., Lam, F., Proud, C., et al. Targeting Mnks for cancer therapy. Oncotarget 3(2), 118-131 (2012).
57. Gkogkas et al (2013) Autism-related deficits via dysregulated eIF4E-dependent translational control. Nature 493 371 PMID: 23172145
58. Moerke et al (2007) Small-molecule inhibition of the interaction between the translation initiation factors eIF4E and eIF4G. Cell 128 257 PMID: 17254965
59. Remington's Pharmaceutical Sciences, 15th Edition.
60. WO2017117052
61. WO2018218038

The invention claimed is:

1. A method of treating migraine in a human subject, comprising administering to the subject an amount of first therapeutic selected from cercosporamide, eFT508, or 4EGI-1 sufficient to treat said migraine.
2. The method of claim 1, further comprising additionally administering to the subject a second therapeutic selected from cercosporamide, eFT508, 4EGI-1, a CGRP inhibitor, a gepant, lasmiditan, a triptan, an ergotamine, an antiemetic, a NSAID or a non-narcotic analgesic, an opiate analgesic, a non-opiate analgesic, a steroid, lidocaine, valproic acid, or propofol.
3. The method of claim 2, wherein the first therapeutic and second therapeutic are co-formulated.
4. The method of claim 2, wherein the first therapeutic and the second therapeutic are not co-formulated.
5. The method of claim 4, wherein the first therapeutic and the second therapeutic are delivered at distinct times.
6. The method of claim 1, wherein the first therapeutic is delivered daily.
7. The method of claim 1, wherein the first therapeutic is delivered upon onset of at least one migraine symptom.
8. The method of claim 3, wherein the first and second therapeutics are delivered daily.
9. The method of claim 3, wherein the first and second therapeutics are delivered upon onset of at least one migraine symptom.
10. The method of claim 4, wherein one of the first therapeutic or second therapeutic is delivered daily, while the other of the first therapeutic or second therapeutic is delivered upon onset of at least one migraine symptom.
11. The method of claim 4, wherein the first therapeutic and second therapeutic are both delivered daily.
12. The method of claim 4, wherein the first therapeutic and second therapeutic are both delivered upon onset of at least one migraine symptom.
13. The method of claim 1, wherein the subject has previously experienced migraine.
14. A composition comprising:
at least two of cercosporamide, eFT508, or 4EGI-1, both in an effective amount to treat migraine in a human subject; and
a pharmaceutically acceptable carrier.
15. A composition comprising:
at least one of cercosporamide, eFT508, or 4EGI-1 and at least one additional migraine therapeutic, both in an effective amount to treat migraine in a human subject; and
a pharmaceutically acceptable carrier.
16. The method of claim 1, wherein the first therapeutic is cercosporamide.
17. The method of claim 1, wherein the first therapeutic is eFT508.
18. The method of claim 1, wherein the first therapeutic is 4EGI-1.

* * * * *